US011024432B2

(12) United States Patent
Chiu et al.

(10) Patent No.: US 11,024,432 B2
(45) Date of Patent: *Jun. 1, 2021

(54) PATIENT EMERGENCY RESPONSE SYSTEM

(71) Applicant: Ross Medical Corporation, Iselin, NJ (US)

(72) Inventors: Alexander Ross Chiu, Oakland, CA (US); Neil Adam Frederick, Fairfax, VA (US); Eric Alan Frederick, Davis, CA (US); Jimmy Young Jae Chung, Lakewood, CA (US)

(73) Assignee: Ross Medical Corporation, Iselin, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/456,194

(22) Filed: Jun. 28, 2019

(65) Prior Publication Data

US 2019/0318827 A1    Oct. 17, 2019

Related U.S. Application Data

(63) Continuation of application No. 14/805,662, filed on Jul. 22, 2015, now Pat. No. 10,380,324, which is a
(Continued)

(51) Int. Cl.
*G16H 40/67* (2018.01)
*H04M 11/04* (2006.01)
(Continued)

(52) U.S. Cl.
CPC ............ *G16H 80/00* (2018.01); *G16H 40/20* (2018.01); *G16H 40/67* (2018.01); *H04L 67/12* (2013.01); *H04L 67/18* (2013.01); *H04M 11/04* (2013.01)

(58) Field of Classification Search
USPC ........................................................ 379/33
See application file for complete search history.

(56) References Cited

U.S. PATENT DOCUMENTS 5,301,105 A    5/1994  Cummings, Jr.
5,911,132 A    6/1999  Sloane
(Continued)

FOREIGN PATENT DOCUMENTS

EP    1011433 B1    2/2009
EP    2415243 A2    2/2012
(Continued)

OTHER PUBLICATIONS

International Search Report and Written Opinion for PCT/US2013/023689 dated Apr. 12, 2013.
(Continued)

*Primary Examiner* — Maria El-Zoobi
(74) *Attorney, Agent, or Firm* — Hansen IP Law PLLC

(57) ABSTRACT

An improved emergency response system is provided. The system includes a patient or subscriber location database having a schedule of patient or subscriber activities. In one implementation, an emergency services server detects when the patient or subscriber is having a possible medical event as indicated by medical physiologic data transmitted from a wireless communication device proximate the patient. A third party such as a technologist and/or doctor diagnoses the patient and determines whether treatment is required. If treatment is required, a phone located remotely from the patient is used to call an emergency services first responder from a public safety access point in the patient's location. The remotely located phone has an automatic location identification database record that is updated based on the patient's current location as indicate by the patient location database. The address information in the patient location database includes street number, building number, floor and
(Continued)

room number information, if applicable, to ensure that first responders are directed to the patient's specific location. Other implementations of the emergency response system are also described, including natural disasters, home security, and travel applications.

25 Claims, 10 Drawing Sheets

Related U.S. Application Data continuation of application No. 13/082,775, filed on Apr. 8, 2011, now abandoned.

(60) Provisional application No. 61/423,484, filed on Dec. 15, 2010.

(51) Int. Cl.
*G16H 80/00* (2018.01)
*H04L 29/08* (2006.01)
*G16H 40/20* (2018.01)

(56) References Cited

U.S. PATENT DOCUMENTS

| | | |
|---|---|---|
| 5,911,667 A | 6/1999 | Sato et al. |
| 5,987,519 A | 11/1999 | Peifer et al. |
| 6,083,248 A | 7/2000 | Thompson |
| 6,102,856 A | 8/2000 | Groff et al. |
| 6,253,210 B1 | 6/2001 | Smith et al. |
| 6,302,844 B1 | 10/2001 | Walker et al. |
| 6,368,284 B1 | 4/2002 | Bardy |
| 6,398,727 B1 | 6/2002 | Bui et al. |
| 6,481,887 B1 | 11/2002 | Mirabella |
| 6,579,242 B2 | 6/2003 | Bui et al. |
| 6,708,184 B2 | 3/2004 | Smith et al. |
| 6,827,690 B2 | 12/2004 | Bardy |
| 6,830,549 B2 | 12/2004 | Bui et al. |
| 7,174,335 B2 | 2/2007 | Kameda |
| 7,299,087 B2 | 11/2007 | Bardy et al. |
| 7,412,396 B1 | 8/2008 | Haq |
| 7,426,475 B1 | 9/2008 | Tangellapally et al. |
| 7,440,567 B2 | 10/2008 | Wellons et al. |
| 7,789,828 B2 | 9/2010 | Clapp |
| 7,826,598 B1 | 11/2010 | Prozeniuk et al. |
| 7,987,100 B2 | 7/2011 | Brown |
| 8,019,622 B2 | 9/2011 | Kaboff et al. |
| 8,131,566 B2 | 3/2012 | Dicks et al. |
| 8,355,934 B2 | 1/2013 | Virdhagriswaran |
| 2001/0014597 A1* | 8/2001 | Takiguchi ............ G01S 19/17 455/343.2 |
| 2001/0051765 A1 | 12/2001 | Walker et al. |
| 2002/0099275 A1 | 7/2002 | Schmidt et al. |
| 2003/0177034 A1 | 9/2003 | Oka et al. |
| 2003/0177035 A1 | 9/2003 | Oka et al. |
| 2003/0177036 A1 | 9/2003 | Oka et al. |
| 2003/0177037 A1 | 9/2003 | Oka et al. |
| 2003/0177177 A1 | 9/2003 | Oka et al. |
| 2004/0015056 A1 | 1/2004 | Shinoda |
| 2004/0184584 A1* | 9/2004 | McCalmont ............ H04M 3/42 379/45 |
| 2004/0190497 A1* | 9/2004 | Knox .................. H04Q 3/66 370/352 |
| 2005/0075116 A1* | 4/2005 | Laird .................. H04W 4/029 455/456.3 |
| 2005/0083911 A1 | 4/2005 | Grabelsky et al. |
| 2006/0106290 A1 | 5/2006 | Bulat |
| 2006/0159235 A1 | 7/2006 | Eisner et al. |
| 2006/0224413 A1 | 10/2006 | Kim et al. |
| 2006/0227959 A1* | 10/2006 | Mitchell ............ H04M 3/42059 379/221.13 |
| 2006/0293024 A1 | 12/2006 | Benco et al. |
| 2007/0060097 A1* | 3/2007 | Edge .................. H04W 8/205 455/404.1 |
| 2007/0298765 A1 | 12/2007 | Dickinson et al. |
| 2008/0200143 A1 | 8/2008 | Qiu et al. |
| 2008/0285544 A1 | 11/2008 | Qiu et al. |
| 2008/0288293 A1 | 11/2008 | Brown, Jr. |
| 2009/0003312 A1 | 1/2009 | Velazquez et al. |
| 2009/0018882 A1 | 1/2009 | Burton et al. |
| 2009/0074175 A1 | 3/2009 | Wellons et al. |
| 2009/0181638 A1 | 7/2009 | Gottlieb |
| 2009/0186596 A1* | 7/2009 | Kaltsukis ............ G08B 25/08 455/404.2 |
| 2009/0198733 A1 | 8/2009 | Gounares et al. |
| 2009/0247634 A1 | 10/2009 | Schechter |
| 2009/0292555 A1 | 11/2009 | Brown |
| 2009/0322513 A1 | 12/2009 | Hwang et al. |
| 2010/0056875 A1 | 3/2010 | Schoenberg et al. |
| 2010/0131434 A1 | 5/2010 | Magent et al. |
| 2010/0166154 A1 | 7/2010 | Peters |
| 2010/0204596 A1 | 8/2010 | Knutsson |
| 2010/0204999 A1 | 8/2010 | Scarola |
| 2011/0071363 A1 | 3/2011 | Montijo et al. |
| 2011/0086609 A1* | 4/2011 | Buehler .............. H04W 4/029 455/404.2 |
| 2011/0106557 A1 | 5/2011 | Gazula |
| 2011/0112416 A1 | 5/2011 | Myr |
| 2011/0144451 A1 | 6/2011 | Robertson |
| 2011/0213620 A1 | 9/2011 | Dziubinski |
| 2014/0028783 A1* | 1/2014 | Kaltsukis ............ G08B 25/001 348/14.08 |

FOREIGN PATENT DOCUMENTS

| | | |
|---|---|---|
| JP | 09135816 A | 5/1997 |
| JP | 11213066 A | 8/1999 |
| JP | 2002132958 A | 5/2002 |
| JP | 2003016195 A | 1/2003 |
| JP | 3493847 B2 | 2/2004 |
| JP | 2008234109 A | 10/2008 |
| JP | 4549361 B9 | 7/2010 |
| WO | 0211614 A2 | 2/2002 |
| WO | 2010055409 A2 | 5/2010 |
| WO | 2010114257 A2 | 10/2010 |
| WO | 20130116243 A1 | 8/2013 |

OTHER PUBLICATIONS

English translation of JP3493847, from Lexis Nexis Total Patent.
English translation of JP11213066, from Lexis Nexis Total Patent.
English translation of JP2008234109A, from Lexis Nexis Total Patent.
English translation of JP2002132958A, from Lexis Nexis Total Patent.
English translation of JP4549361, from Lexis Nexis Total Patent.
English translation of JP09135816, from Lexis Nexis Total Patent.
English translation of JP2003016195, from Lexis Nexis Total Patent.
English abstract of EP 2415243A2 from Lexis Nexis Total Patent.
International Preliminary Report on Patentability for PCT/US2013/023689 dated Aug. 14, 2014.
International Preliminary Report on Patentability (IPRP) for PCT/US2011/057229 dated Dec. 17, 2012.
As-Filed Petition for new IPRP for PCT/US2011/057229 on Jan. 11, 2013.
Decision to Petition for PCT/US2011/057229 dated Feb. 11, 2013.
Corrected International Preliminary Report on Patentability (IPRP) for PCT/US2011/057229 dated Mar. 1, 2013.
International Search Report and Written Opinion for PCT/US2011/057229 dated Apr. 25, 2012.
Steve Taylor and Larry Hettick; "How E9-11 caller locations are discovered;" http://www.networkworld.com/newsletters/converg/2005/1114converge1.html Network World (Nov. 14, 2005).
"Logistic Regression," Wikipedia.
National Emergency Number Association (NENA) Technical Committee Chairs; "NENA Standard Data Formats for ALI Data Exchange & GIS Mapping;" NENA-02-010, Version 8.2 (Jun. 10, 2009).

(56) References Cited

OTHER PUBLICATIONS

Public Safety and Homeland Security Bureau; "PSAP Registry," http://www.fcc.gov/pshs/services/911-services/enhanced911/psapregistry.html (Nov. 3, 2010).
Public Safety and Homeland Security Bureau; "Enhanced 9-1-1-Wireless Services;" http://www.fcc.gov/pshs/services/911-services/enhanced911/Welcome.html (Nov. 3, 2011).
Jerry Foree; "E911 Master Street Adress Guide (MSAG) Development and Maintenance;" (Aug. 2008).
Extended European Search Report (eESR) for EP Patent App. No. 11 849 770.0 dated Oct. 27, 2016.
As-filed response to Extended European Search Report (eESR) for EP Patent App. No. 11 849 770.0 dated May 23, 2017.
Extended European Search Report for EP 20165998.4 dated Jun. 22, 2020.

* cited by examiner

Patient Location Database

| Name | Date | Time | Street No. | Street Name | Building Number | Floor Number | City | State | Appointment |
|---|---|---|---|---|---|---|---|---|---|
| John Doe | September 19, 2010 | 1:30 pm | 2345 | Hogan | 1 | 1 | Warren | MI | Transit from Home to Cardiologist |
| John Doe | September 19, 2010 | 2:00 pm | 1062 | Maple | 1 | 3 | Troy | MI | Cardiologist |
| John Doe | September 19, 2010 | 3:00 pm | 1062 Maple | | 1 | 3 | Troy | MI | Transit from Cardiologist to Home |
| John Doe | September 19, 2010 | 3:30 pm | 2345 | Hogan | 1 | 1 | Warren | MI | Transit from Home to ECG facility |
| John Doe | September 20, 2010 | 4:00 pm | 3456 | Wayne | 3 | 8 | Royal Oak | MI | ECG |
| John Doe | September 20, 2010 | 4:30 pm | 3456 | Wayne | 3 | 8 | Royal Oak | MI | Transit from ECG facility to home |

FIG. 2

Treatment Facility Database

| Name 94a | Street Number 94b | Street Name 94c | City 94d | State 94e | Building 94f | Floor 94g | Services 94h | Schedule for Services 94i |
|---|---|---|---|---|---|---|---|---|
| Royal Oak Beaumont Hospital | 3601 | W. 13 Mile Road | Royal Oak | MI | D | 2 | Cardiac Surgery | M-Sa 9am-11pm |
| Huron Valley Sinai Hospital | 1 | William Carls Drive | Commerce Township | MI | 1 | Ground | Cardiac Catheterization Lab | M-Sa 10am-2am |
| Henry Ford Hospital Heart & Vascular Institute | 2799 | W. Grand Blvd. | Detroit | MI | 1 | 1 | Cardiac Catheterization Lab | M-Su 24 hours |

PATIENT EMERGENCY RESPONSE SYSTEM

CROSS-REFERENCE TO RELATED APPLICATIONS

This application is a continuation of U.S. patent application Ser. No. 14/805,662, filed Jul. 22, 2015, which is a continuation of U.S. patent application Ser. No. 13/082,775, filed Apr. 8, 2011 which claims the benefit of U.S. Provisional Patent Application No. 61/423,484, filed on Dec. 15, 2010, the entirety of each of which is hereby incorporated by reference.

FIELD

This disclosure relates to emergency response systems, and more particularly, to emergency response systems with improved methods for dispatching emergency services personnel to a specific location at which a patient or subscriber is located.

BACKGROUND

As health care costs continue to rise, it becomes increasingly desirable to minimize the length of time patients must be hospitalized while still ensuring that they receive the appropriate degree of care. Many standard treatment protocols require patients to undergo continual testing and monitoring that may diagnose medical problems and emergencies. For example, many patients with heart problems require stress testing and monitoring. However, to reduce costs, it is desirable to conduct such testing and monitoring in facilities that lack physicians or equipment to perform emergency medical services should the patient experience a medical event, such as a heart attack or stroke. Such testing could be performed in hospitals, however, doing so reduces the number of suitable testing facilities and requires increased patient travel. In addition, outside of hospital facilities many of the personnel who perform such outpatient testing lack the diagnostic skills to determine if a patient is experiencing a medical event requiring treatment and may not be present with the patient when an event occurs. Thus, a remotely located technologist and/or physician is required to determine whether the patient needs treatment, and if so, identify a suitable treatment facility.

In one scenario, it would be desirable to provide patients with physiologic testing devices that monitor their condition and which alert medical personnel to a possible medical event. Some devices that are capable of wirelessly transmitting patient physiologic data to a remote server, such as via the internet, exist. However, even though the server may be programmed to determine if such data is indicative of a medical event, there is no reliable way for remote medical personnel to select a suitable treatment facility and contact the public safety access point (PSAP) in the patient's geographic location to dispatch first responders to the patient's specific location. In addition, if the patient is unconscious or unable to communicate, his or her geographic location may be difficult to ascertain. In certain situations, a cellular telephone in the patient's possession or near the patient may be used to determine the patient's location for purposes of dispatching medical personnel. However, such devices are typically accurate to within 300 meters, a level of accuracy which is typically not sufficient reliable to ensure that first responders can quickly locate the patient. Thus, a need has arisen for an improved patient emergency response system.

SUMMARY

In accordance with a first aspect, a system for providing emergency services to a patient is provided which comprises a phone located remotely from the patient and an emergency services server programmed to generate an updated automatic location identification database record for the phone based on the patient's location. In certain embodiments, the phone is a VoIP (voice over internet protocol) phone. In other embodiments, the emergency services server is programmed to generate a master street address guide address for the patient's location, and the updated automatic location identification database record includes the master street address guide address.

In additional embodiments, the emergency services sever is programmed to determine the patient's location based on a time stamp. In further embodiments, the emergency services server is programmed to determine the patient's location by comparing the patient time-stamp to a plurality of database time entries corresponding to the patient and determining whether any of the plurality of database time entries corresponding to the patient are within a pre-selected time increment from the patient time-stamp. In still other embodiments, the patient time-stamp corresponds to one selected from radiolocation coordinates and global positioning system coordinates transmitted by a wireless communication device proximate the patient. In yet other embodiments, the system further comprises a patient location database comprising a plurality of database time entries and a plurality of database patient locations, wherein each of the database time entries corresponds to a patient, and each database patient location corresponds to a database patient time entry.

In other embodiments, the system further comprises a treatment facility database including a plurality of database treatment facilities, and database treatment facility locations, database treatment facility services, and database treatment facility schedules corresponding to each of the database treatment facilities. In another aspect, a system for providing emergency medical services is provided which comprises a phone having an associated automatic location identification database record, wherein the automatic location identification record contains location information for the phone. The system also comprises a patient location database, comprising database patient identity information for a plurality of patients and one or more database patient locations for each patient from among the plurality of patients. The system further includes an emergency services server programmed to determine a patient location based on preliminary patient location information, database patient identity information, and the one or more database patient locations corresponding to the patient, wherein the emergency services sever generates an updated automatic location identification database record for the phone based on the determined patient location or a user-entered patient location. In certain embodiments, the emergency services server is programmed to generate a master street address guide address for the patient's location, and the updated automatic location information database record includes the master street address guide address.

In an additional aspect, a method of providing improved emergency services is provided.
The method comprises receiving a patient's medical physiologic data indicating the occurrence of a medical event, determining the patient's location, and updating an automatic location identification database record for a phone based on the patient's location, wherein the phone is located remotely from the patient. In certain embodiments, the method further comprises entering a predetermined emergency services number into the phone, thereby placing a call to a public safety access point corresponding to the updated automatic location identification database record. In other embodiments, the step of determining the patient's location comprises determining the patient's location based on a patient time-stamp corresponding to one selected from radiolocation coordinates and global positioning system coordinates. In additional embodiments, the step of determining the patient's location comprises determining if the patient's time stamp is within a pre-selected time increment from a database time entry corresponding to the patient. In other embodiments, the method comprises selecting a treatment facility based on at least one selected from the group consisting of the patient's location, facility location information, the patient's medical condition, and a time-stamp corresponding to one selected from radiolocation coordinates and global positioning system coordinates.

In yet another aspect, a method of determining a patient's location is provided. The method comprises providing a patient time-stamp, providing a schedule of patient activities, wherein the schedule comprises a plurality of scheduled times, each time corresponds to a scheduled location, and each scheduled location comprises a master street address guide location, and receiving a preliminary location for the patient. The method further comprises selecting a scheduled location based on the time-stamp and the preliminary location. In certain embodiments, the step of selecting a scheduled location based on the time-stamp and preliminary location comprises selecting a first scheduled time, the first scheduled time is within a selected time increment from the time-stamp, and the first scheduled time corresponds to a first scheduled location. In other embodiments, the first scheduled location is within a selected distance from the preliminary location. In other embodiments, the selected distance is no greater than about 600 meters.

BRIEF DESCRIPTION OF THE DRAWINGS

Referring now to the drawings, illustrative embodiments are shown in detail. Although the drawings represent some embodiments, the drawings are not necessarily to scale and certain features may be exaggerated, removed, or partially sectioned to better illustrate and explain the present invention. Further, the embodiments set forth herein are exemplary and are not intended to be exhaustive or otherwise limit or restrict the claims to the precise forms and configurations shown in the drawings and disclosed in the following detailed description.

FIG. 2 is a depiction of database records from a patient location database;

FIG. 3 is a depiction of database records from a treatment facility database;

DETAILED DESCRIPTION

Figure 1A:
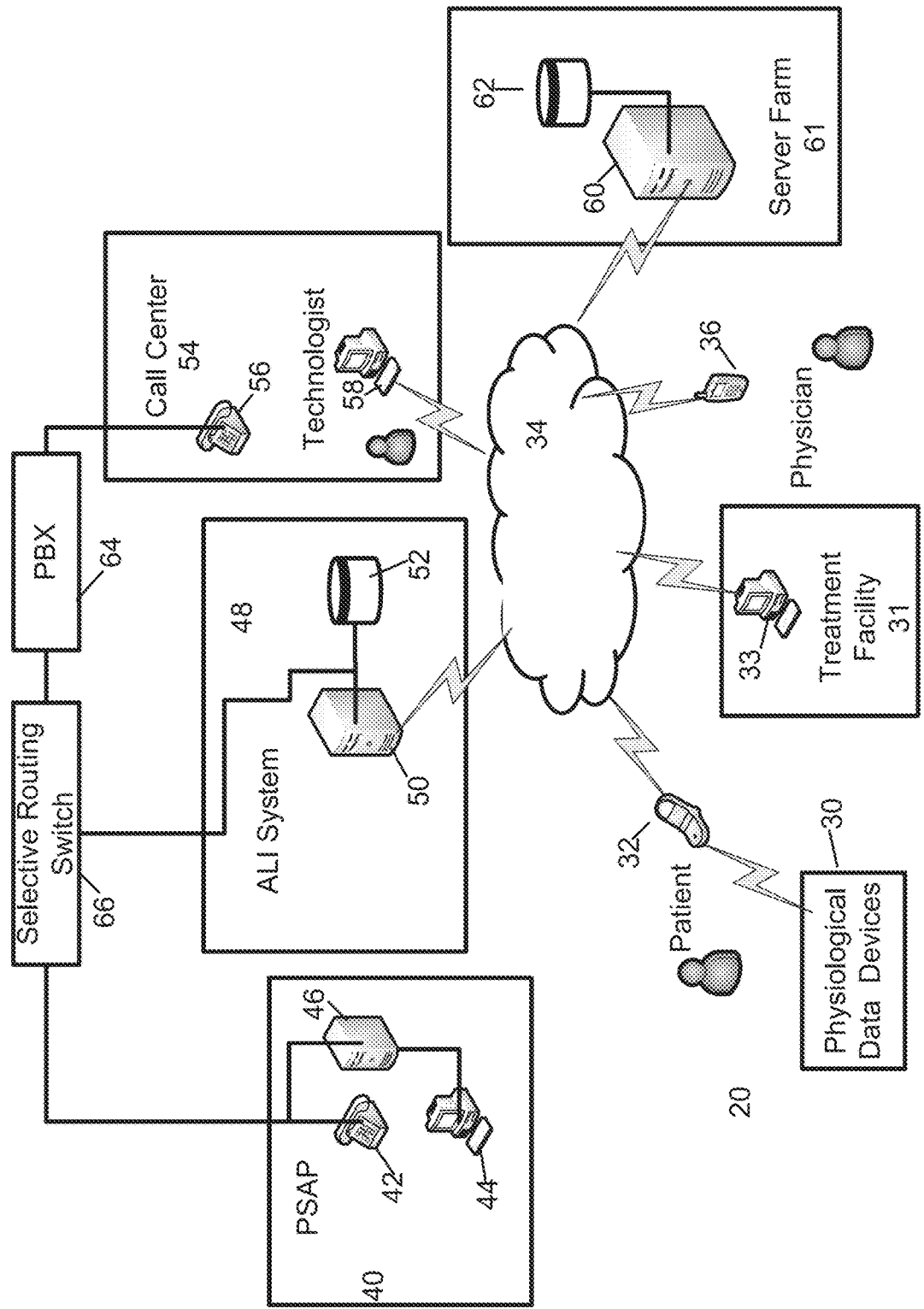
FIG. 1A is a depiction of a first embodiment of an improved system for providing emergency services.

Referring to FIG. 1A, a system 20 for providing emergency services to a patient with a medical condition is provided. System 20 comprises one or more physiological data devices 30 used to make various physiological measurements of the patient, an emergency services server farm 61, a call center 54, an automatic location identification ("ALI") system 48, a public safety answering point or "PSAP" 40, a Private Branch Exchange or "PBX" 66, and a selective routing switch 66. System 20 also includes a computer network 34, which is preferably a wide area network ("WAN") and even more preferably the internet. As discussed in greater detail below, system 20 allows a technologist located in call center 54 to make an emergency services call to obtain emergency services for the patient. The call will generally be made using an emergency services number such as 9-1-1 (U.S.), 9-9-9 (U.K.), 1-1-2 (Germany, Denmark, Iceland, Sweden). In some jurisdictions, there are multiple emergency services numbers depending on the nature of the requested emergency services (police, ambulance, or fire).

In certain implementations, the technologist will make an emergency services call from call center phone 56, and the call will be routed to the PSAP 40 responsible for the jurisdiction in which the patient, not the call center 54, is located. In additional implementations, the PSAP 40 will receive data indicating the patient's location by querying an ALI database 48 record associated with the call center phone 56. In other implementations, information transmitted from the patient to the technologist in call center 54 will be "geocoded" to provide an address—such as a full MSAG (master street address guide) address—which is more accurate than those provided by many current systems. The call center phone may be a landline, VoIP phone, or a cell phone, but is preferably a landline or VoIP phone.

PSAP 40 dispatches the necessary emergency responders (fire, police, ambulance) to the patient in response to a voice call, and in some examples, in response to patient location data related to the voice call. A PSAP will typically include several PSAP operators each with a terminal 44 and a phone 42. Only one phone 42 and terminal 44 are shown in FIG. 1A. A PSAP 40 will typically also include at least one PSAP server 46 to facilitate the transmission, receipt, and storage of data related to emergency calls.

ALI system 48 comprises one or more servers 50 and one or more databases 52. The ALI system stores location information for emergency services callers and provides it to PSAP 40 to better enable the PSAP 40 to dispatch the necessary emergency responders to the correct location, especially where the caller cannot communicate with the PSAP (e.g., due to unconsciousness). In typical known systems, the PSAP 40 receives a voice call and a telephone number associated with the call known as an "ANI" or "Automatic Number Information" value. In certain implementations, in particular those used for wireless and/or VoIP calls, the ANI is referred to as a "pseudo-ANI" or "p-ANI."

The p-ANI is a string of digits, such as the ten digits in a phone number, which may be used to encode the caller's location, as may be indicated by a cell tower and sector or latitude/longitude. As used herein, the term "ANI" refers to a standard ANI (telephone number) or a p-ANI.

In certain jurisdictions which use enhanced 9-1-1 systems, when the PSAP receives an emergency services call, it then transmits the ANI back to the ALI system 48 and requests the caller's location (a process sometimes called "bidding" or "dipping"). The ALI system database 20 includes fields that correspond ANI or p-ANI values to a physical location (e.g., street address, city, state). An ALI data record for the caller is then transmitted back to the PSAP terminal 44 via PSAP server 46 to better enable the PSAP to dispatch emergency services to the location identified by the ALI record. In jurisdictions with older 9-1-1 systems, ALI system 48 may not exist, and ALI records may not be provided to the PSAP 40.

System 20 is particularly useful for patients who must be closely monitored and routinely tested due to a known medical condition, such as cardiac disease, diabetes, etc. The range of medical conditions for which system 20 may be used is not limited. In one implementation, a patient subscribes to use system 20 and is associated with one or more call centers 54 used to monitor the patient's after care following his or her release from a medical facility. Call center 54 is staffed with one or more technologists who monitor the subscribing patients' medical conditions by tracking physiological data transmitted from the patient to the call center 54 via computer network 34. Call center 54 may comprise a single building or a plurality of buildings, which may be co-located or geographically disperse. The technologists in call center 54 receive information concerning potential medical events being experienced by the patients they serve and diagnose the patient's condition based on the received data and/or based on communications with the patient. The technologists may also enlist the aid of a physician or other third party to provide diagnostic assistance. Based on the results of such diagnoses, the technologist may contact PSAP 40 to dispatch emergency responders to the patient's location to provide needed medical attention and/or transport the patient to a treatment facility 31 where such attention can be provided. System 20 may be used with a wide variety of medical events and is not limited to any particular event or events. Non-limiting examples of such events include acute coronary syndrome, myocardial ischemia, myocardial infarction, cardiac arrhythmia, syncope, congestive heart failure, pulmonary edema, stroke, transient ischemic attack, elevated intracranial pressure, seizure, and carbon monoxide poisoning.

In system 20, one or more physiological data devices 30 are provided which detect physiological data for a patient and transmit the data to a communication device 32 via either wireless or wired connections. Communication device 32 then transmits the physiological data to technologist terminal 58, server farm 61, physician communication device 36, and/or treatment facility terminal 33 via computer network 34. A variety of known physiological data devices 30 may be used to measure physiological data such as ECG data, implantable cardioverter defibrillator data, blood vessel impedance data, intra-cardiac pressure sensor data, ultrasound data, intracranial pressure sensor data, pulse oximetry data, co-oximeter sensor data, light absorbance data, glucometer data, EEG data, and endovascular graph sensor data, to name a few. Suitable physiological data devices 30 configured to transmit data to communication device 32 include those supplied by Card Guard Scientific Survival, Ltd., of Rehovot, Israel and QRS Diagnostic of Maple Grove, Minn. Other suppliers of such physiological data devices include Nasiff Associates, Inc. of Central Square, N.Y. and Pulse Biomedical, Inc. of Norristown, Pa. For wireless implementations, the physiological data devices 30 will preferably include a wireless transmitter configured to wirelessly transmit data to patient communication device 32. Wireless communications between physiological data devices 30 and patient communication device 32 may be provided using various protocols and other wireless technologies, including 3G and 4G wireless technologies and the IEEE series of wireless technologies. More particularly, wireless communications may take place over a CDMA, EDGE, EV-DO, GPRS, GSM, UMTS, W-CDMA, or a 1×RTT network as well as an IEEE 802.11 (WiFi), 802.15 (Bluetooth and Zigbee), 802.16 (WiMax) or 802.20 (MBWA) network.

Patient communication device 32 acts as a gateway to computer network 34. Suitable communication devices 32 will be capable of wirelessly communicating with one or more internet servers, in particular, emergency services servers 60, located in emergency services server farm 61. Suitable communication devices 32 include wireless transmitters and include cellular telephones, smart phones, tablet computers, laptop computers, desktop computers with wireless modems, etc.

In cases where wireless transmission between patient communication device 32 and computer network 34 cannot be achieved or is transient—such as in the case of the patient living in the basement or out of wireless range—an additional device, such as a wireless router, can be integrated to send the data via wired transmission to internet cloud 34. One such exemplary router is the GAC 150 WiFi dial up router supplied by Great Arbor Communications of Potomac, Md. In such cases, the patient plugs the router into a phone jack or an existing Ethernet port. When the reception is weak the patient communication device will switch to WiFi and look for the router signal. If the router is connected to an Ethernet port, it will transfer the data through the patient's own wired internet connection (e.g., home broadband cable or DSL connection). If the router is connected to the phone line, when the router senses a WiFi connection from the phone, it automatically dials the "dial up services" to get a 54K dial up connection.

In other cases, a patient may live in a rural area without phone or internet service. In such cases, the patient is provided with a wireless network extender that connects to patient communication device 32 via WiFi and is able to transmit data and voice over satellite. In this scenario, the patient communication device 32 preferably has a direct line of sight to the sky (i.e., a window).

Technologist terminal 58 is configured to communicate with server farm 61 via computer network 34 and to receive patient physiological data therefrom. Terminal 58 may include a processor and one or more stored programs for performing various types of displays and/or analyses of retrieved physiological data as well as for retrieving patient information, such as patient identity information, patient location information, patient schedule information, patient medical history information, patient medications, etc.

ALI system 50 is generally a known type of ALI system used in enhanced 9-1-1 systems and is configured to provide an address data record to PSAP 40 based on an ANI or p-ANI value received from the PSAP 40. The ALI may serve a large geographic area and will not generally be limited to those patients served by call center(s) 54. The specificity of the address information contained in any particular ALI record may vary and may include a street name, street number, city name, and state name. The ALI record may also include cell phone radiolocation coordinates (a cell tower site and sector) and global positioning system coordinates (e.g., a longitude and latitude). In certain implementations described herein, ALI records may be supplemented to include further specific patient location information such as a building number (e.g., an internal address within a complex of buildings), a floor number, and a room number. In certain jurisdictions a "master street address guide" or "MSAG" may exist which is an official record of valid streets, thoroughfares, house numbers and communities in the jurisdiction, and the ALI database 52 records may include MSAG addresses. In other implementations involving next generation 911 (NG911) systems, the ALI record may be further supplemented to include video, voice, pictures, floorplans, and medical information data.

Call center 54 is connected to PSAP 40 via PBX 64 and selective routing switch 66. PBX 64 is a private telephone network used within an enterprise or company, and its users share outside lines for making telephone calls external to the PBX 64. Selective routing switch 66 and ALI System 48 are typically operated by an emergency services provisioning provider. PBX 64 determines whether a particular voice call is an emergency services call or a non-emergency services call. If the call is an emergency services call, the selective routing switch 66 routes the call to a selected PSAP 40, which is preferably the PSAP 40 servicing the jurisdiction in which the patient is located at the time the patient experiences a potential medical event. Selective routing switch 66 utilizes a selective routing database (SRDB) (not shown) to route the call to the PSAP servicing the location defined by the ALI information.

Certain known SRDBs for landline applications use the ANI associated with an emergency call (i.e., the telephone number from which the call is made) to determine the correct PSAP to which the call should be routed. In certain existing applications for landline emergency callers, the ANI is uniquely associated with the caller's address in the ALI database 52 and the ANI can be used to properly route the emergency call. However, in certain implementations of system 20, call center phone 56 will be used to place the emergency services call, despite being located remotely from the patient. In known systems, the use of the call center phone 56 ANI to route the call would cause the call to be routed to the PSAP in the jurisdiction in which the call center 54 is located, instead of that in which the patient is located.

In one implementation of system 20, the SRDB (not shown) correlates ANI and p-ANI values to PSAPs. In this implementation, the correlation between ANI/p-ANI and PSAP is dynamically updated based on the location of the patient so that a call from phone 56 is routed to the PSAP 40 in the same jurisdiction as that location. In this manner, calls originating from call center phone 56 will appear to the PSAP to have originated from the patient's location instead of the call center 54 location. When a technologist in call center 54 determines that emergency services should be dispatched to a patient, the patient's current location may also be used to create an updated ALI record for call center phone 56.

In another implementation of system 20, "location-based" routing is used. In this implementation, the SRDB (not shown) correlates ALI locations to PSAPs. In certain examples, the PSAPs geographic boundaries are used to determine which PSAP is responsible for the caller's location. Thus, once the ALI record for the call center phone 56 is updated based on the patient's location, the SRDB (not shown) uses that updated ALI record to select the appropriate PSAP 40. The selective routing switch 66 then routes the call to the selected PSAP 40. In this implementation, there is no need for a database that correlates ANI values to PSAPs. The SRDB (not shown) does not need to be dynamically updated based on the caller's location because the PSAPs geographic boundaries are static (with the exception of infrequent changes made by the government). However, regardless of whether ANI-based routing or location-based routing is used, selective routing switch 66 effectively uses the patient's location to route the call placed by call center phone 56 to a PSAP 40 responsible for the patient's location.

System 20 is particularly useful for situations in which the patient is unable to make an emergency services call or is unable to access a landline with a fixed ANI and ALI record. Cell phones and VoIP phones do not have fixed locations, and thus do not have fixed ALI records or fixed associations between a PSAP and an ANI. Known methods for routing emergency services calls placed from cellular telephones exist. However, the location information transmitted from a cellular telephone, such as GPS coordinates or radiolocation coordinates, is generally only accurate to within +/−300 meters, a level of accuracy which may make it impossible for emergency responders to locate the patient or at least to locate the patient quickly enough to provide the necessary medical treatment. Accordingly, in system 20, the technologist uses call center phone 56 to place the emergency services call for the patient. Emergency services database 62 includes location information for the patient which is preferably more accurate than that provided by global positioning system or radiolocation coordinates. This location information is used to update the ALI record for call center phone 56 and transmit the updated record to ALI system server 50, which then updates ALI database 52 with the patient's current location. The SRDB (not shown) uses the updated patient location information to determine the PSAP 40 to which the call will be routed. As indicated previously, this may involve updating a table that correlates ANIs to PSAPs (ANI-based routing) or it may involve using the updated ALI record to determine which PSAP's geographic boundaries encompass it (location-based routing). In those jurisdictions in which an ALI database is available, the PSAP 40 then queries the ALI system 48 with the call center phone's 56 ANI. Based on the ANI, the ALI server 50 queries the ALI database 52 to obtain the location record associated with the ANI (a process known as "bidding" or "dipping") and transmits it to PSAP 40 for display on the PSAP terminal 44, thereby allowing the PSAP operator to dispatch emergency responders to the correct patient location. In certain implementations, selective routing switch 66 may comprise a sever capable of transmitting data and voice signals to PSAP 40, and the ALI record may be transmitted with the call, thus eliminating the need for a subsequent ALI database 52 query.

Certain existing selective routing systems may be used to update an ALI record and correctly route an emergency services call based on the location information retrieved from the emergency services database 62 (i.e., location-based routing). One system is provided by Dash Carrier Services and is referred to as a "Dynamic Geospatial Routing" system. In one example, the selective routing switch 66 uses a map database which correlates PSAPs and their telephone numbers to geographic locations. The map database may be part of the SRDB (not shown) and can be used with the patient location information provided by the emergency services server 60 to identify the correct PSAP 40 to which selective routing switch 66 will route the call.

As indicated in FIG. 1A, the call center technologist may also communicate with a physician's smart phone 36 by providing data from the emergency services server 62 to it. In addition, system 20 may be configured to allow the physician to directly access a patient's data from emergency services server 62. This allows the technologist to consult with a physician about the patient's condition and obtain diagnostic and/or treatment advice from the physician. In some cases, however, the technologist may have sufficient information to make a diagnosis or determine that emergency responders should be dispatched to the patient without consulting with a physician.

In certain implementations of system 20, one or more treatment facility terminals 33 for one or more treatment facilities 31 are also connected to network 34, allowing the technologist to communicate data about a patient and/or a medical event to the treatment facility to aid in determining if the facility has the necessary staff and facilities to address the patient's medical event.

Figure 1B:
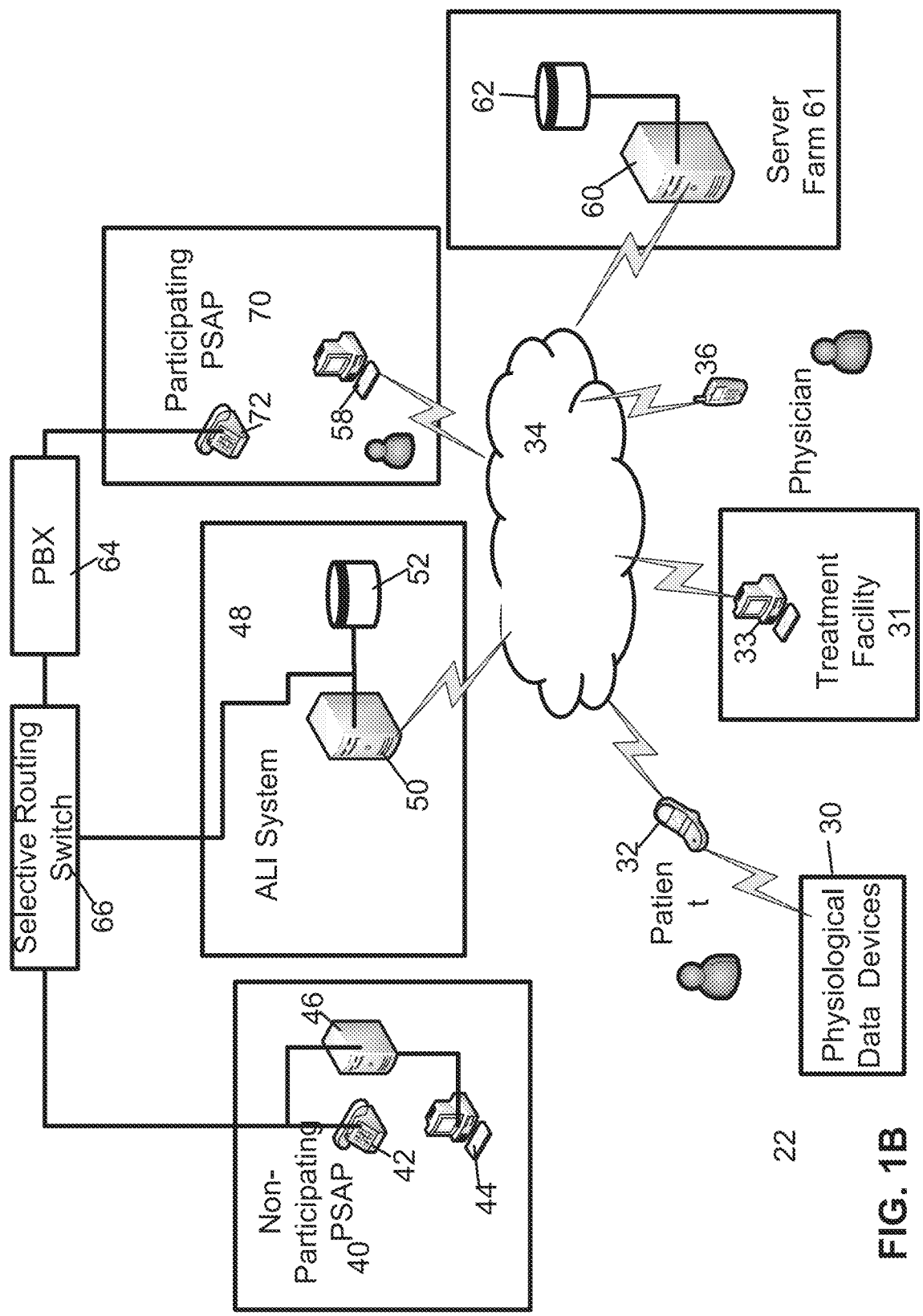
FIG. 1B is a depiction of a second embodiment of an improved system for providing emergency services.

Referring to FIG. 1B, an alternate embodiment of a system 22 for providing emergency patient services is provided. System 22 is configured similarly to system 20, and like components are identified with like numerals. However, in system 22 no separate call center 54 or technologists are provided. Instead, certain PSAPs are designated as "participating PSAPs" 70 and perform the same function as the call center 54 and technologists of system 20 in FIG. 1A. The participating PSAPs 70 receive patient physiological data transmitted from physiological data devices 30 and function in the same manner as the call center 54 technologists of FIG. 1A. If a participating PSAP 70 is alerted to a medical event for a patient in its jurisdiction, it can access patient location data from emergency services server farm 61 and dispatch the emergency responders to the correct location. However, if the Participating PSAP 70 is not in the same jurisdiction as the patient, it can then transmit patient location information retrieved from the emergency services server 62 to the ALI system 48 and cause the ALI record for the PSAP 70 phone to be updated based on the patient's location. The participating PSAP 70 operator can then dial the emergency services number from participating PSAP phone 72, causing the selective routing switch 66 to route the call to the Non-Participating PSAP 40 servicing the patient's location. The Non-Participating PSAP 40 then queries the ALI database to obtain the ALI record for phone 72, which corresponds to the patient's location, not that of phone 72. Based on this information, the Non-Participating PSAP 40 can dispatch emergency responders to the patient's location.

Figure 1C:
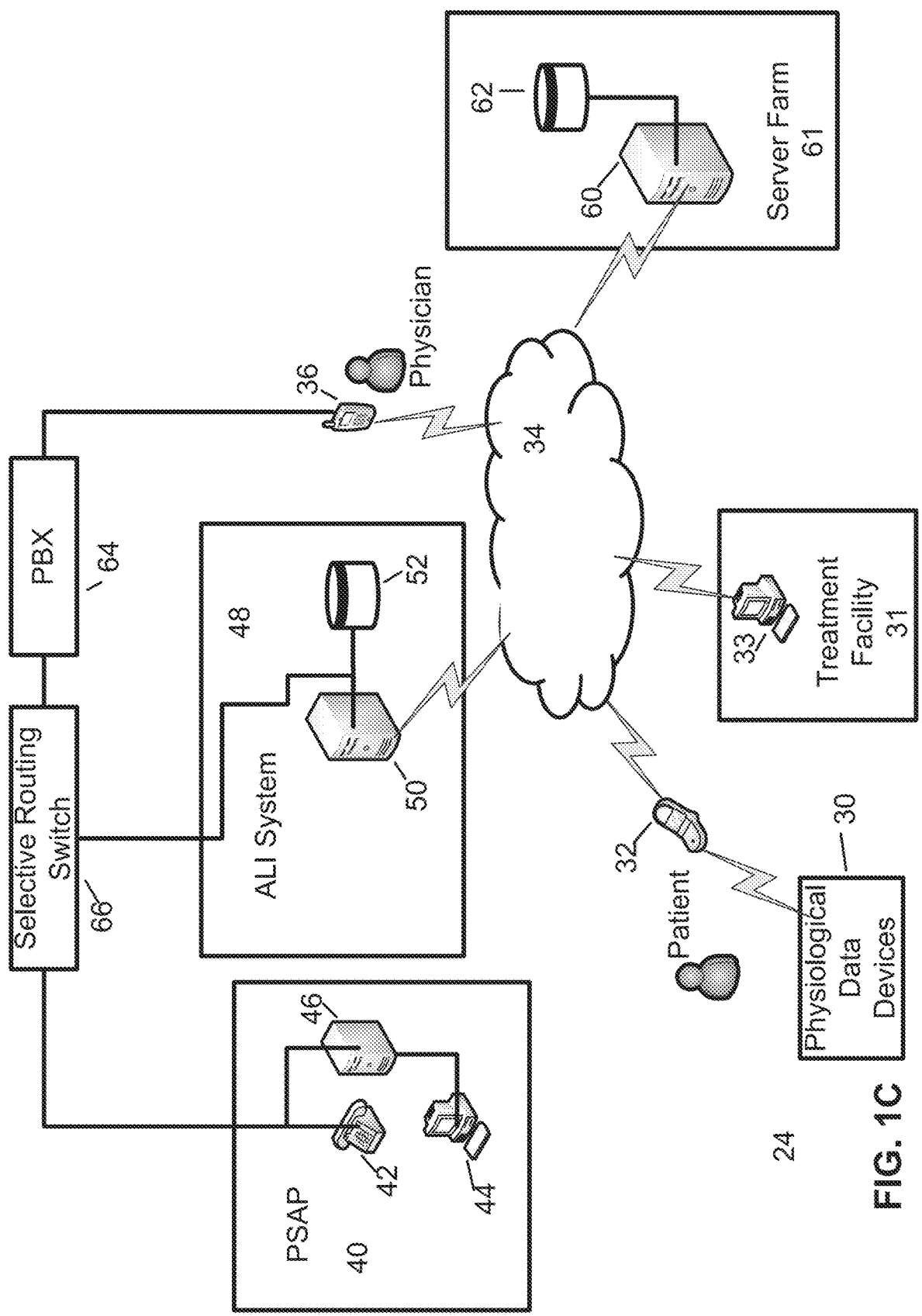
FIG. 1C is a depiction of a third embodiment of an improved system for providing emergency services.

Another embodiment of system 24 for providing emergency patient services is depicted in FIG. 1C. In this embodiment, call center 54 is not used. Instead, emergency services calls are placed by the physician using physician's communication device 36, which is preferably a smart phone. Physician's communication device 36 is connected (wirelessly) to PBX 64. Physician's communication device 36 is programmed to transmit an updated ALI record for device 36 to ALI system 50 so that the ALI record associated with physician's communication device 36 corresponds to the patient's location. Selective routing switch 66 routes the call based on the updated ALI record to the PSAP servicing the patient's location.

As indicated above, systems 20, 22, and 24 allow an emergency services call placed from a phone 56, 72, 36 (respectively) which is located remotely from a patient to be routed to the PSAP responsible for the patient's jurisdiction, rather than the jurisdiction in which the phone 56, 72, 36 is physically located. As described below, in certain implementations, the patient's location is "geocoded" or linked to certain information transmitted from the patient, such as a time-stamp transmitted from the patient's communication device 32.

Emergency services server farm 61 includes one or more emergency services databases 62. Emergency services databases 62 may include a variety of different databases related to providing emergency services. Depicted in FIG. 2 is a patient location database 80 used in the geocoding of patient locations. Patient location database 80 includes a plurality of records 82a-82f and a plurality of fields 84a-84j for each record. In the example of FIG. 2, patient location database 80 includes schedule information for one or more patients, although only one patient (John Doe) is used to illustrate the database 80. Each patient's records (82a-82g) define a scheduled event in the daily activities of the patient. Thus, field 84a provides the name of the patient. Field 84b provides the date (or day of the week) of a scheduled activity. Field 84c provides the time of a scheduled activity. Fields 84d-84i collectively define a patient location for a scheduled activity. In certain preferred embodiments, fields 84d-84i collectively define the Master Street Address Guide (MSAG) address at which the scheduled activity takes place. In the example of FIG. 2, field 84a includes a street number, field 84b includes a street name, field 84g provides a building number (as in the case of a multi-building complex), and field 84g provides a floor number. Fields 84h and 84i respectively include the city and state of the scheduled event. If appropriate, other patient location fields may be included. For example, in some implementations, the patient may be in a large building with a number of rooms or offices, and a field for the number of the room or office in which the scheduled event takes place may also be included. Other fields which may be provided include the phone number of the location, a contact person and company associated with the scheduled event, the duration of the scheduled event with a variance (e.g., +/−5 mins), a variance for the scheduled time, and the date the scheduled time (or other information in a given record) was last updated. As illustrated in records 82a, 82c, 82d, and 82f, in some situations the event will be a transfer of the patient from one location to another. Transfers may also include other fields specific to transfers such as route data and the transit company.

Field 84j provides information about the nature of the scheduled event or appointment. In the example of FIG. 2, the scheduled events include cardiologist appointments and ECG test appointments, as well as transit events to and from those appointments. In certain implementations, patient location database 80 is used with patients who have been recently discharged from a medical facility and who undergo routine testing to monitor their condition. Such patients may undergo testing which itself can lead to the occurrence of a medical event. Much of this testing may occur outside of medical facilities that can provide emergency medical care, and as a result, system 20 (or 22) may be used to dispatch emergency responders to the patient's testing location, if necessary.

For example, patients who suffer from cardiac disease may undergo scheduled stress tests at regular intervals, which could cause a medical event such as a myocardial infarction to occur. With rising medical care costs, it is desirable to treat and monitor patients outside of a hospital setting. However, this approach presents the risk that the patient will undergo a medical event which requires emergent care. In such cases, it is beneficial to have a well-defined patient location in the patient location database 80 so that emergency responders can quickly respond to the emergency. Systems 20, 22, and 24 can be used to improve emergency responder response times and better ensure that the patient is quickly located and transported to an appropriate treatment facility 31 tailored to the patient's medical event. Patient location database 80 allows technologists in call center 54 (or participating PSAPs 70) to determine the patient's location and route an emergency call to the correct PSAP with a level of accuracy that would not be available unless the patient placed the emergency services call from a landline, something that may not be possible during an emergency event. For example, if the patient were to call 9-1-1 from a cellular telephone, the call would be routed (and the ALI record for the phone 56 would be updated) based on the patient's global positioning system coordinates or radiolocation coordinates. These location identification techniques are known to be accurate to a level of no greater than 300 meters. Even when landlines are used, the patient may be at an internal location in a large building or complex which is not specifically identified in the ALI database. As a result, emergency responders may not be able to find the patient in time to transport him or her to the appropriate treatment facility. As will be discussed further below, in certain embodiments systems 20 and 22 are configured to so that during a medical event the technologist or participating PSAP receives the geocoded address from fields 84d-84i in the patient location database 80. The technologist then causes the emergency services server 60 to transmit that information to the ALI system 48 to update the ALI record for the call center phone 56 (or participating PSAP phone 72) with the patient's geocoded address. The selective routing switch 66 uses the updated ALI record to route the call to the PSAP responsible for the patient's location (as indicated by the geocoded address). Systems for dynamically updating ALI records are commercially available, and include those provided by suppliers such as Intrado, RedSky, Dash CS, and 8×8, Inc.

In certain implementations, the emergency services database(s) 62 include a treatment facility database 90. An exemplary depiction of a treatment facility database 90 is provided in FIG. 3. Treatment facility database 90 includes information that enables the technologist or participating PSAP 70 to identify and select treatment facilities to which a patient should be transported in the case of a medical event. The process of identifying a correct treatment facility may be based on a number of factors, some of which may include the treatment facility's location, the treatment facility's equipment and capabilities, the time of the day, and the availability of certain treatment facility staff. Treatment facility database 90 includes a plurality of records 92a-92c each of which corresponds to particular treatment facilities. Treatment facility database 90 also includes a plurality of fields 94a-94i which include a variety of information about each treatment facility. For example, in FIG. 3, fields describing the name of the treatment facility 94a and treatment facility location (fields 94b-94g) are provided. The treatment facility location information in fields 94b-94g may correspond to the facility's MSAG address in certain implementations. In the specific example of FIG. 3, the treatment facility location information in treatment facility database 90 includes a street number 94b, street name 94c, city 94d, state 94e, building 94f (as in the case of a multi-building complex), and floor 94g. Although not illustrated in FIG. 3, a given medical building or complex may have several internal treatment facilities. Separate records may be provided for each distinct internal facility to better ensure that the patient is routed to the correct internal location. For example, a given hospital may have a surgery wing and a cardiac catheterization lab, which may be some distance from one another within the hospital. In that case, treatment facility database 90 may include two records for the hospital, one of which pertains to the surgery wing and another which pertains to the cardiac catheterization lab. Additional fields may also be provided which include some or all of the following: treatment center phone numbers, treatment center fax numbers, treatment center e-mail addresses, on-call physician pager numbers and e-mail addresses, FTP links for transmitting medical data to/from the treatment center, and a date/time when information was last updated.

Figure 4:
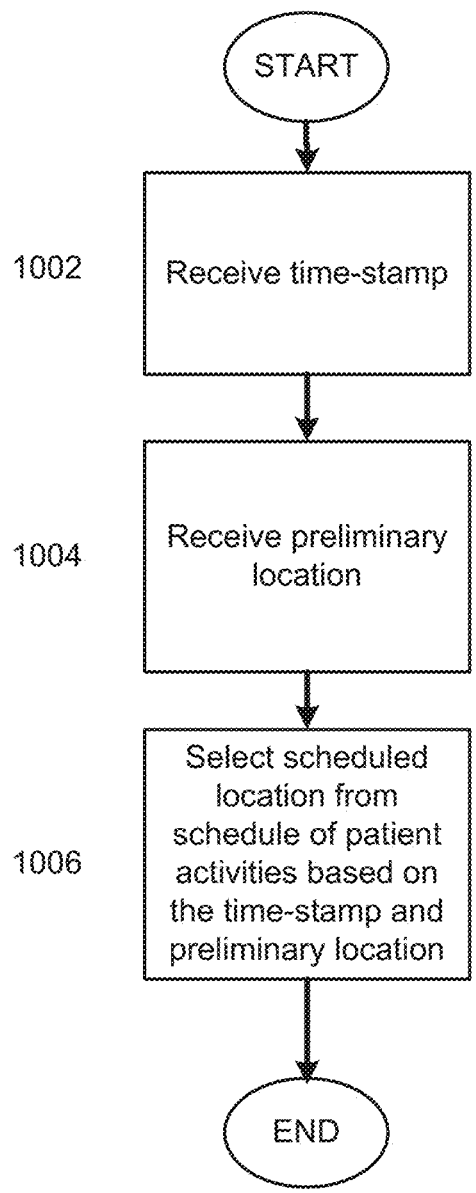
FIG. 4 is a flow chart used to illustrate a first embodiment of a method of determining a patient or subscriber's location.

In certain examples, emergency services server 60 (which may comprises a plurality of servers) is programmed to identify a patient location based on the information included in patient location database 80, for example, by performing a database query operation of patient location database 80. In certain cases, the technologist initiates the query from call center terminal 58. FIG. 4 illustrates an exemplary method that may be used by emergency services server 60 to perform the query operation. As illustrated in the figure, in step 1002 the emergency services server 60 receives a time-stamp, i.e., data indicative of a date, day of the week, and/or time of day. The emergency services server 60 also receives a preliminary location information for the patient. In certain examples, the preliminary location information will include global positioning system coordinates or radiolocation coordinates for the patient's communication device 32. Based on the time-stamp and the preliminary location information, the program executed by emergency services server 60 will obtain a scheduled location from patient location database 80. In some circumstances, the preliminary location information may not be available, in which case the program will select a scheduled location for the patient based on the time-stamp only. In other circumstances, the time stamp may be the time that the emergency services server 60 receives an alarm or other indication that a medical event may be occurring, as opposed to a time-stamp received directly from a patient communication device 32.

Figure 5:
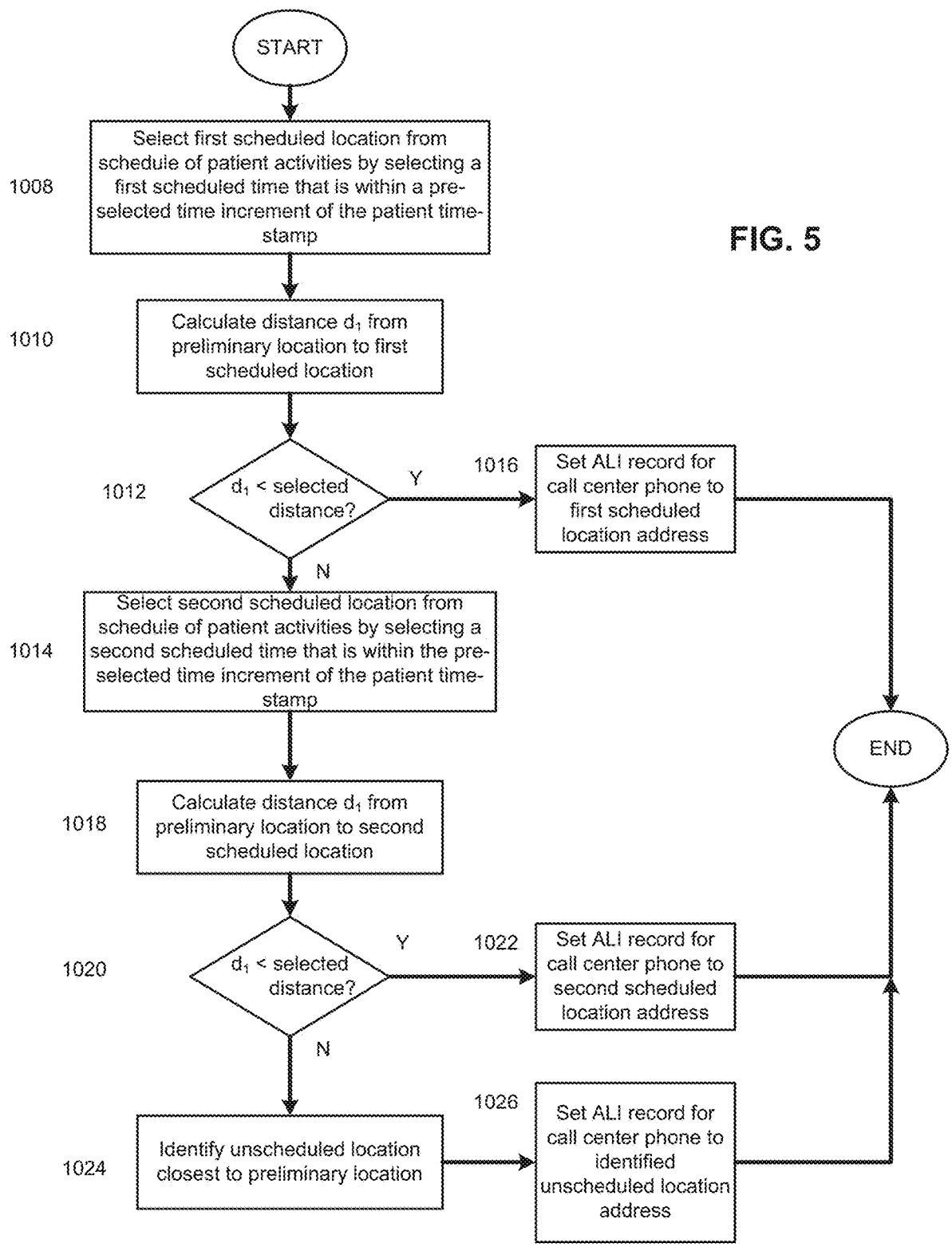
FIG. 5 is a flow chart used to illustrate a second embodiment of a method of determining a patient or subscriber's location.

A variety of methods may be used to select a patient location from the patient location database 80 based on a time-stamp and preliminary location information. Once such method is depicted in FIG. 5. In accordance with the method, in step 1008 a first scheduled location is selected from a schedule of patient activities by selecting a first scheduled time that is within a pre-selected time increment of the patient time-stamp. Referring to the exemplary patient location database of FIG. 2, a time-stamp corresponding to 1:45 pm on Sep. 19, 2010 is within a 30 minute time increment of both the event identified in record 82a (transit from home to cardiologist) and the event identified in record 82b (cardiologist appointment). At 1:45 pm, the patient may still be in transit to the cardiologist or he or she may have arrived at the cardiologist's office.

Using the patient's preliminary location information (e.g., GPS or radiolocation coordinates), in step 1010 a distance $d_1$ is calculated from the preliminary location to the first scheduled location. In one embodiment, a straight line distance between the two locations is calculated. The distance $d_1$ is preferably less than about 600 m, more preferably less than about 300 m, more preferably less than about 100 m, and even more preferably less than about 30 m. In step 1012, it is determined whether the calculated distance $d_1$ is less (or no greater) than a selected distance. This step is used to determine whether the first scheduled location is likely where the patient actually is. If $d_1$ indicates that the patient is likely to be in the first scheduled location, in step 1016 the ALI record for the call center phone 56 is updated to match the location information for the first scheduled event. In ANI-based routing solutions, the PSAP responsible for the location in which the first scheduled event occurs is associated with the ANI for the call center phone 56 in the SRDB (not shown) so that the selective routing switch 66 will route the call to that PSAP. Step 1016 may be implemented in a number of different ways. In one implementation, the location information for the first scheduled event is transmitted to technologist terminal 58 to allow the technologist to determine whether the location is believed to be reliable. The technologist can then use terminal 58 to initiate transmission of the location information to ALI server 50 for storage in the ALI database 52. This will cause emergency services calls placed from phone 56 to be routed to the PSAP servicing the patient's geocoded location. The PSAP 40 will then query the ALI system 48 for the address corresponding to call center phone 56, and ALI system 48 will transmit the patient's scheduled event location to the PSAP terminal 44.

In step 1012, if the calculated distance $d_1$ is greater (or no less than) the selected distance, in step 1014, a second scheduled location is selected which also has a scheduled time within the preselected time increment of the patient time-stamp (if such a scheduled event exists). In step 1018, the distance $d_1$ is calculated between the second scheduled location and the patient's preliminary location. If $d_1$ is less than (or no greater than) the selected distance, control proceeds to step 1022, causing the ALI record for the call center phone 56 to be updated to the second scheduled location specified in the patient location database 80 as with step 1016. In step 1020, if $d_1$ is greater than (or not less than) the selected distance, control is transferred to step 1024 and an unscheduled location is selected which is closest to the preliminary location.

Although not depicted in FIG. 2, the patient location database 80 may include a variety of known locations at which a patient may be present at any given time, although the locations are not associated with any particular scheduled event. In step 1024, the program calculates the distance between the patient's preliminary location and each unscheduled location, and the unscheduled location which is the closest to the patient's preliminary location is selected. In step 1026, the ALI record for call center phone 56 is updated to match the unscheduled location. In ANI-based routing solutions, the PSAP 40 responsible for the unscheduled location is associated with the ANI for the call center phone 56 in the SRDB (not shown). In certain implementations, the unscheduled locations are MSAG addresses. Unscheduled locations may include places such as relative's/friend's residences, supermarkets, banks, post offices, restaurants, bars, theaters, sporting arenas, or any other locations the patient is known to frequent. If no unscheduled location corresponds to the time-stamp received by emergency services server 60, the patient's preliminary location information (e.g., GPS or radiolocation coordinates) is used as the patient's geocoded location. The ANI for the call center phone is then associated with the PSAP responsible for that geocoded location, and the ALI record associated with the ANI is updated to the geocoded location.

Figure 6:
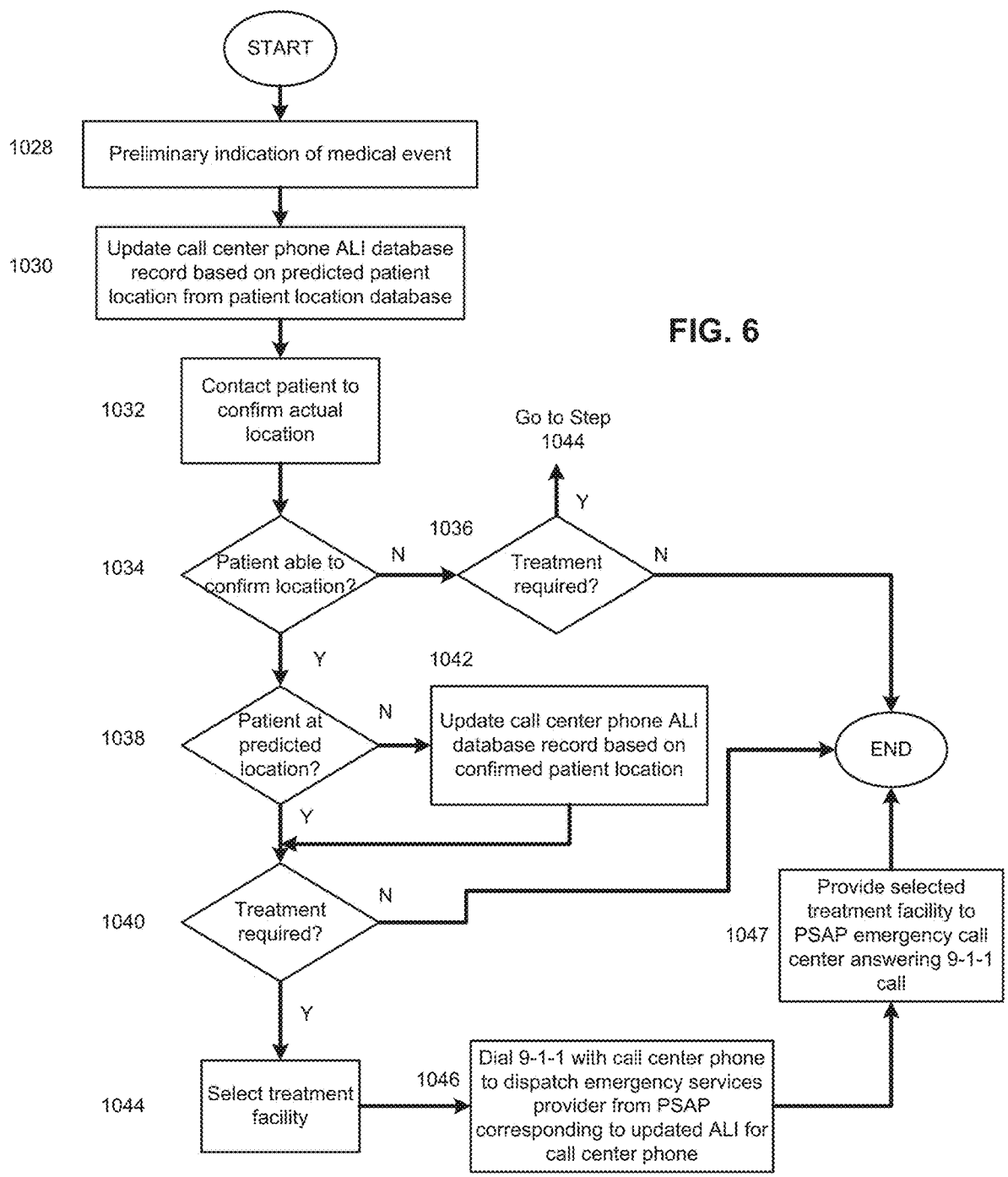
FIG. 6 is a flow chart used to illustrate an embodiment of a method of providing emergency services to a patient or subscriber.

In certain implementations, it may be desirable to have the call center 54 technologist confirm the patient's location during a suspected medical event to ensure that location information obtained from the patient location database 80 is accurate. If the patient's location differs from that predicted by the patient location database 80, the technologist may use the confirmed location to update the ALI record for the call center phone 56. It may also be desirable to include a process for selecting a treatment facility 31 that is best able to handle the patient's medical event. An exemplary method that includes these features is described in FIG. 6. In step 1028, the technologist receives a preliminary indication of a medical event from the patient. As discussed previously, in one example, the indication may be provided by a message or alarm generated by emergency services server 61 and transmitted to technologist terminal 58. The alarm or message may be based on values of physiological data generated by physiological data devices 30 and transmitted from patient communication device 30 to emergency services server 60. In step 1030, the ALI database 52 record for the call center phone 56 (or participating PSAP phone 72) is updated based on a predicted patient location obtained from the patient location database 80. One exemplary method for carrying out step 1030 is the method described in FIG. 5.

In step 1032, the technologist uses the call center phone 56 to contact the patient on his or her communication device 32. In addition, the technologist may use other forms of communication such as e-mail and text messages, depending on the particular communication device 32 used by the patient. The technologist then asks the patient to confirm his or her location. If the patient is unconscious or otherwise unable to confirm his or her location, control proceeds to step 1036. In step 1036, the technologist determines whether the patient requires treatment based on a variety of selected factors, which may include the patient's physiological data generated by the physiological data devices 30 (the current data and/or historical data) and patient medical history data, which may also be stored for retrieval on the emergency services database 62. Step 1036 may also involve consulting with a physician on physician communication device 36. If no treatment is required, the process ends.

If treatment is required, control transfers to step 1044. In step 1044, the technologist selects a treatment facility 31 to which the patient will be transported by emergency responders. The selection of the treatment facility may involve querying the treatment facility database 90 to identify the most suitable treatment facility 31 based on one or more criteria selected from the patient's location, the facility activation time (i.e., how long it takes for the facility to have the required services available), the treatment facility location, the treatment facility equipment and services, and the treatment facilities current staffing. In step 1046, the technologist uses the call center phone 56 to dial the emergency services number (e.g., 9-1-1 in the United States). Based on the updated ALI record, the selective routing switch 66 routes the call (and ANI or p-ANI) to the PSAP 40 in the same jurisdiction as the patient's predicted location. PSAP 40 then queries the ALI system 48 with the ANI and is provided with the patient's predicted location on PSAP terminal 44, allowing emergency responders to be dispatched thereto. When the emergency services call is answered, the technologist can inform the PSAP operator of the selected treatment facility to which the patient should be taken.

To illustrate the selection of the treatment facility 31, assume that the patient has a medical event that is believed to involve the blockage of a coronary artery and that the technologist alone or in consultation with a physician has determined that a stent is required to relieve the blockage. If the medical event occurs on a Sunday at noon, the cardiac catheterization lab for the facility in record 92b of FIG. 3 will be unavailable. However, the cardiac catheterization lab for the facility in record 92c will be available. Thus, the technologist would request that PSAP 40 direct emergency responders to transport the patient to the facility specified in field 94a of record 92c.

Figure 7:
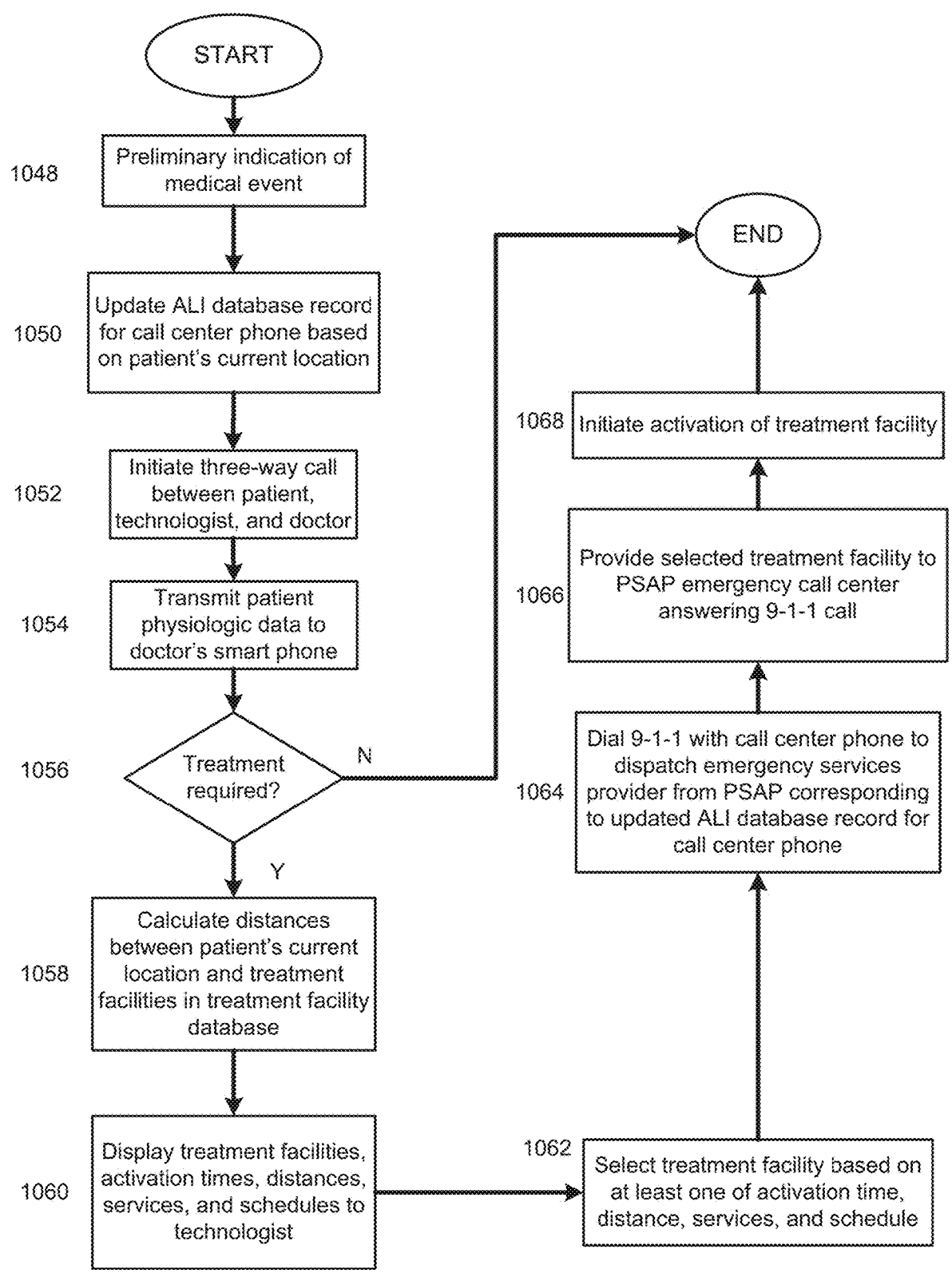
FIG. 7 is a flow chart used to illustrate a method of selecting a treatment facility for a patient experiencing a medical event.

Another exemplary method for using systems 20 or 22 to provide emergency services to a patient is described in FIG. 7. Referring to the figure, in step 1048 the technologist receives a preliminary indication of a medical event, which could simply be a communication (phone call, text message, e-mail) received from the patient or someone proximate the patient and/or a message or alarm provided by the emergency services server 60 due to physiological data generated by physiological data devices 30.

In step 1050, the PSAP associated with the patient's current location is associated with the ANI for the call center phone 56 in the relevant database associated with selective routing switch 66. The ALI record for call center phone 56 (or participating PSAP phone 72) is updated so that its location is the patient's current location. The examples of FIGS. 4 and 5 depict exemplary methods of obtaining the patient's current location. In step 1052, the technologist initiates a three-way telephone call with the patient (using patient communication device 32) and a physician (using physician communication device 36). To better enable the physician to assist in diagnosing the patient's potential medical event, in step 1054 the technologist causes the patient's physiologic data to be transmitted from emergency services server 60 to the physician communication device 36, which in this example would be a laptop, smartphone, or some other device capable of receiving data transmissions from computer network 34.

In step 1056, the physician and/or technologist determine whether the patient requires treatment. If the patient does not require treatment, the process ends. If the patient does require treatment, the technologist will execute a program on the emergency services server 60 to calculate distances between the patient's current location and the location of the various treatment facilities (e.g., those specified by records 92a-92c) in FIG. 3. In step 1060, a list of treatment facilities and the distances from the patient to them are displayed on the technologist terminal 58 along with additional information about the treatment facilities, such as some or all of the information in fields 94a-94i of FIG. 3. In step 1062, a treatment facility is selected based on one or more criteria selected from activation time, distance (from the patient), services, and schedule. This selection process may be wholly or partially automated using a program resident executed by a processor that is local to the technologist terminal 58 or local to the emergency services server 60.

In step 1064, the technologist uses call center phone 56 (or the participating PSAP uses call center phone 72) to dial an emergency services number (e.g., 9-1-1 in the United States). In step 1050, the ALI database record for the phone 56 is updated to the patient's location and the ANI for the call center phone 56 is associated with a PSAP 40 servicing the jurisdiction in which the patient is located. Thus, the call placed in step 1064 is routed with the ANI to the now-associated PSAP 40, which then uses the ANI to query the ALI database 52 and obtain the patient's location.

In step 1066, the technologist (or participating PSAP 70 in the case of a patient using system 22 who is in a jurisdiction serviced by a non-participating PSAP 40), identifies the selected treatment center 31 (from step 1062) to the PSAP operator who then dispatches the appropriate emergency responders to the patient's location. In step 1068, the technologist contacts the selected treatment facility 31 to activate the services necessary to attend to the patient's medical event in accordance with the diagnosis developed in step 1054.

Figure 8:
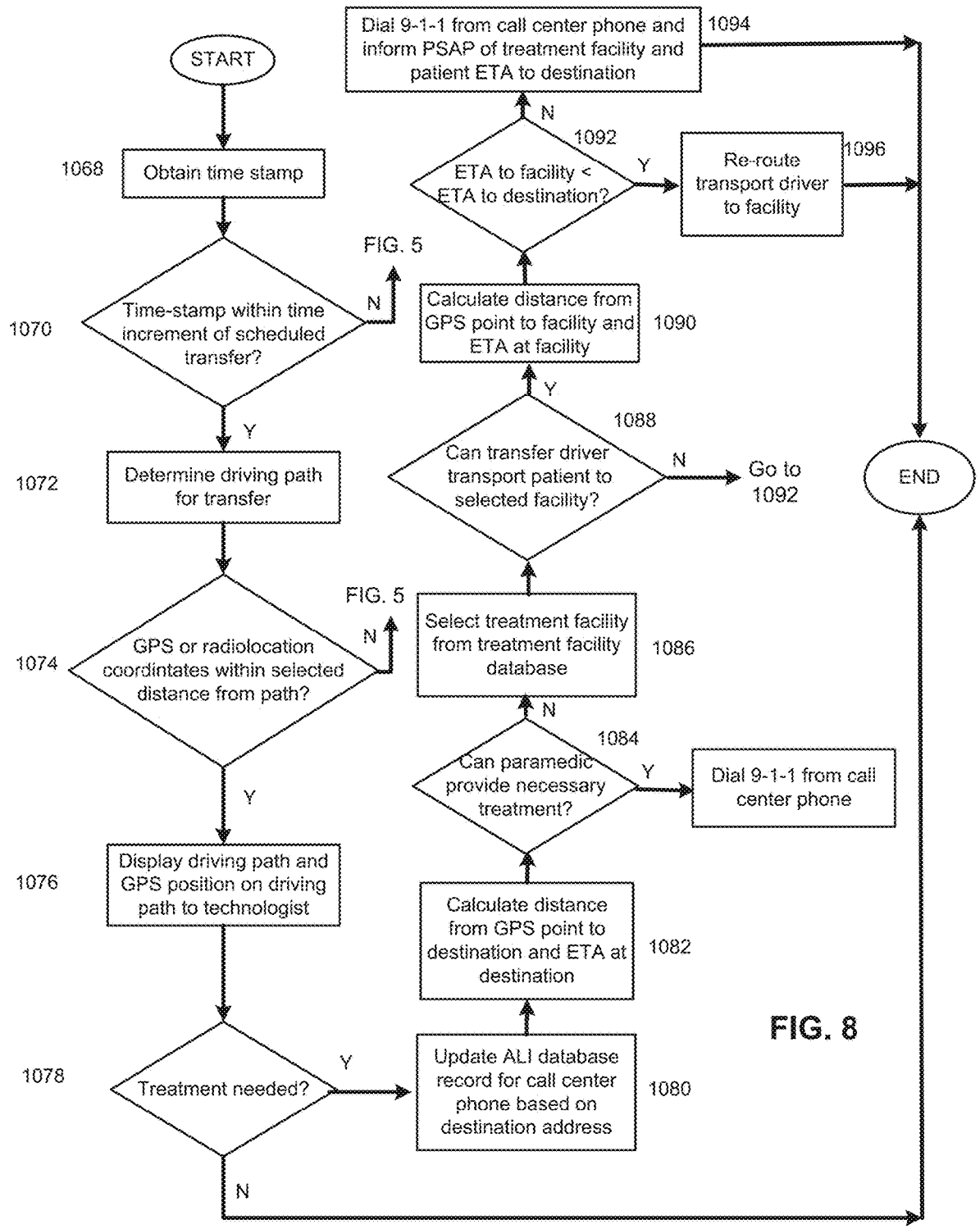
FIG. 8 is a flow chart used to illustrate a method of providing emergency services to a patient being transferred from one location to another.

In certain cases, the patient location database 80 may indicate that the patient's most likely location is in transit from one fixed location, as in the example of record 82a of the patient location database 80. If the patient requires treatment, it may be desirable to have the current transfer driver reroute the patient to a selected treatment facility 31. In other cases, it may be desirable to dispatch emergency responders to the patient's destination to transport him or her to a treatment facility 31. One method of providing emergency patient services for a patient who experiences a potential medical event while in transit between scheduled appointments is described in FIG. 8. In accordance with the figure, in step 1068 the technologist receives a time-stamp from the patient's communication device 32. The time stamp may be associated with physiological data transmitted to the emergency services server 60. The technologist need not receive the time-stamp directly from the patient, but instead, may receive a stored value of the time-stamp which is associated (in a database file or a medical data database contained within the emergency services database 62) with physiological data that caused the emergency services server 60 to generate an alarm or other message indicating the occurrence of a potential medical event.

In step 1070, a program resident on emergency services server 60 queries the patient location database 80 to determine if the time stamp received in step 1068 is within a selected time increment (e.g., 15 minutes, 30 minutes, 45 minutes, or 1 hour, etc.) of a scheduled transit event (transfer). If it is not, the method of FIG. 5 or another method may be used to obtain a patient location associated with a scheduled or unscheduled event described in the patient location database.

In step 1072, the technologist uses terminal 58 to run a program resident on emergency services server 60 which calculates the driving path for the patient's transit event based on initial location and final locations indicated by the patient location database 80. For example, record 82a in patient location database 80 defines a transit event from the patient's home to a cardiologist's office. Thus, the addresses of the patient's home and the cardiologist's office, which would also be stored in the patient location database, are used to calculate a distance between the two locations. In one example, an electronic map database (e.g. Google maps) is used to calculate the distance.

In step 1074, it is determined whether global positioning or radiolocation coordinates provided by the patient's communication device 32 are within a selected distance (e.g., 5 m, 10 m, 20 m, etc.) from the path defined between the patient's starting and end points. If the coordinates are not within the selected distance, another method (e.g., the method of FIG. 5) may be used to determine the patient's location, which may be at a fixed address. If the patient's global positioning or radiolocation coordinates are within the selected distance from the driving path, control transfers to step 1076, and the driving path and patient location are displayed on technologist terminal 58.

In step 1078, the technologist determines if treatment is required in the manner described previously. If no treatment is required, the process ends and the patient continues the transit operation to his scheduled destination. If treatment is required, in step 1080 the ALI database record for the technologist phone 56 is updated to the address of the patient's destination. Thus, returning to the example of record 82a in FIG. 2, the cardiologist's office address (which may preferably be an MSAG address) will be used as the new ALI database location for the phone 56. The SRDB (not shown) will use the updated ALI record to route the call (and ANI) to the PSAP responsible for the cardiologist office's jurisdiction.

In step 1082, a program resident on emergency services server 60 is used to calculate a distance from the patient's location (as indicated by his or her global positioning system or radiolocation coordinates) to the destination and an estimated time of arrival at the destination.

In some cases, a paramedic may have the requisite training and equipment to treat the patient. In such cases, it may be desirable to have the paramedic meet the patient at the scheduled destination (e.g., the cardiologist's office in the example of record 82a in FIG. 2). Thus, in step 1084 it is determined whether the paramedic can provide the necessary treatment. In certain cases, the determination will be made by the technologist and in others it will be made by a physician or jointly by a technologist and physician. If the paramedic can provide the necessary treatment, the technologist uses technologist phone 56 to dial an emergency services number. Selective routing switch 66 routes the call to the PSAP 40 responsible for the jurisdiction in which the patient's destination (e.g., cardiologist's office) is located. The PSAP 40 then queries the ALI database 52 to obtain the address, which in certain implementations is an MSAG address. The PSAP 40 then dispatches a paramedic to the patient's destination.

If the paramedic cannot provide the necessary treatment, control transfers to step 1086. In step 1086, a treatment facility 31 is selected from the treatment facility 31 database 90 in the manner described previously. At this point, it may be possible for the patient's current transit driver to transport the patient to the selected treatment facility 31. Otherwise, it may be desirable to dispatch an emergency responder to transport the patient. Thus, in step 1088, it is determined whether the patient's current transit driver can transport him or her to the selected treatment facility 31.

If the patient's current driver can transport him or her to the selected treatment facility 31, control transfers to step 1090. In step 1090, a program resident on emergency services server 60 calculates the distance from the patient's current location (as indicated by global positioning or radiolocation coordinates) to the selected treatment facility 31 and the estimated time of arrival at the selected treatment facility 31. If the estimated time of arrival at the treatment facility 31 is less than (or no greater than) the estimated time of arrival at the destination (step 1092), the technologist contacts the transit driver (such as calling him or her with technologist phone 56) and instructs him to re-route the patient to the selected treatment facility 31 (step 1096).

If the estimated time of arrival at the treatment facility 31 is greater than (or no less than) the estimated time of arrival at the scheduled destination (e.g., the cardiologist's office), the technologist uses technologist phone 56 to dial an emergency services number (step 1094). Selective routing switch 66 routes the call to the PSAP 40 responsible for the jurisdiction in which the patient's destination is located. PSAP 40 then dispatches emergency responders to the patient's scheduled destination to transfer him or her to the selected treatment facility 31. As indicated by the foregoing, if the patient's transit driver can transport the patient to the treatment facility 31 more quickly than he can transport the patient to his destination, he does so. Otherwise, paramedics (who can provide life support during transit) meet the patient at the scheduled destination and transport him. Accordingly, the method of FIG. 8 balances the considerations of speed and in-transit life support to optimize the patient's treatment for the medical event of concern.

In some instances, none of the scheduled or unscheduled locations or transit events in the patient location database 80 will be close enough to the patient's preliminary location (as indicated by global positioning or radiolocation coordinates) to reliably indicate the patient's current location. In such situations, the method of FIG. 5 may be modified so that the technologist phone 56 ALI record is updated to match the patient's preliminary location information. When the technologist dials the emergency services number, selective router 66 will route the call to the PSAP 40 responsible for the jurisdiction indicated by the patient's preliminary location information. As indicated above, global positioning coordinates and radiolocation coordinates typically have an inherent error of +/−300 meters. As a result, it is preferable to update the technologist phone 56 ALI location record based on a geocoded address from patient location database 80. However, this modified version of the method of FIG. 5 acts as a "fail-safe" when no geocoded address appears to be reliable.

In one further modification, it may be desirable to initiate an emergency services call from the patient's communication device 32 as a fail-safe. For example, if there is a failure in the data transfer from the emergency services server 60 to the ALI system 48, it may not be possible to update the ALI database record for the technologist's phone 56. Accordingly, in one scenario, the technologist uses technologist terminal 58 to communicate with emergency services server 60 and inform server 60 that an emergency services call will be placed. The server 60 transmits instructions to patient communication device 32 which cause device 32 to place an emergency services call and to initiate a three-way call between the answering PSAP 40 and the technologist phone 56. Using standard techniques for the routing of emergency services calls from cellular telephones, the patient's call will be routed to the PSAP 40 responsible for the jurisdiction which includes the global positioning coordinates and/or radiolocation coordinates of patient's communication device 32. The PSAP 40 will then query the ALI system 48 for the patient's global positioning or radiolocation coordinates. However, to improve the accuracy of the patient's location, the technologist will communicate the patient's geocoded address (e.g., the address selected based on the method of FIG. 5) to the PSAP 40 operator. In another variation, the technologist can bypass PSAP 40 and directly contact a public dispatch access point (PDAP) to dispatch a selected emergency responder (e.g., ambulance, police, or fire). The technologist can then communicate the patient's geocoded address to the PDAP. In certain examples, emergency services database 62 will include one or more PDAP databases with addresses, phone numbers and other information related to specific PDAPs.

In certain examples, the server farm 61 will include an alarm server and/or an interpretation server that determines whether physiological data received from physiological data devices 30 indicates a possible medical event. The determination of whether a possible medical event is occurring may be based on the development of patient-specific parameters. In one example, each patient utilizing system 20 or 22 is tested to develop a baseline (non-event) condition for the physiological data relevant to his or her condition. Patient-specific criteria may be developed from past medical event occurrences to determine which deviations from the baseline condition are most likely to indicate a medical event, and those deviations can be used to trigger an alarm transmitted to technologist terminal 58. In certain examples, if an alarm is generated, both the baseline and alarm-triggering measurements may be retrieved from the emergency services server 60 and displayed to the technologist 58.

In certain embodiments, server 60 is programmed to perform a logistic regression method on geocoded location data. In many cases, a technologist will be able to verify the patient's actual location and determine whether (and how closely) it matches the geocoded location provided by the patient location database (e.g. FIG. 2). In certain implementations, the use of a logistic regression method will allow a percentage accuracy to be displayed to the technologist, which indicates the reliability of the geocoded location. In one example, the variables used to perform the logistic regression include the patient's current global positioning coordinates (or radiolocation coordinates) with a time-stamp and the accuracy radius, the patient's schedule of locations, driving directions (e.g., from a computerized map system such as Google Maps), unscheduled locations, verified locations, and unscheduled locations, such as indicated by credit card bills, checks, plane tickets, etc. In one example, the following logistic regression formulae are used to predict the probability that the geocoded location will be correct:

$$f(z)=1+(1+e^{-z}) \tag{1}$$

$$z=\beta_0+\beta_1 x_1+\beta_2 x_2+\beta_3 x_3+ \ldots +\beta_n x_n \tag{2}$$

where $\beta_0, \beta_1, \ldots \beta_n$ are the regression coefficients of $x_1$, $x_2, x_3, \ldots x_n$, which are the independent variables used to predict the patient's location.

In certain examples, the logistic regression formula will "learn" by updating the regression coefficients to improve the accuracy of the prediction.

Systems 20, 22, and 24 as well as the geocoding techniques described herein can be used in a variety of ways other than providing emergency services to patients. For example, systems 20, 22, and 24 could be used to provide dynamic transportable security systems. In one implementation, an alarm system is provided which takes the place of physiological data devices 30 and generates an alarm to the call center 54 indicating that an intrusion or some other security breach has occurred. One known system that is suitable for this purpose is the Quorum A-160 Home Security Monitor. Similar products are also supplied by ASG Security Systems. Subscribers may have their schedules geocoded in a manner similar to that depicted in FIG. 2 so that when an alarm is triggered, a technologist in the call center 54 receives a geocoded address for the subscriber. The geocoded address would then be used to update the ALI database 52 based on the geocoded address. When the call center phone 56 is used to dial an emergency services number, the call will be routed to the PSAP 40 servicing the subscriber's location. In those systems with enhanced 9-1-1 capability, the PSAP 40 can then query the ALI system 48 for the subscriber's location and dispatch police, fire, and/or EMS accordingly.

In another implementation, systems 20, 22, and 24 and the geocoding techniques described herein may be used for search and rescue operations, including during disasters. For example, a plurality of subscribers (instead of patients) may have their schedules geocoded in a subscriber location database included in database 62. The time of occurrence of a disaster and its geographic boundaries may be used by the technologist to determine a list of subscribers who are likely within the disaster zone. Their geocoded locations can be used to update the ALI record of the call center phone 56 so that the relevant PSAP 40 for each of the subscribers may be contacted and dispatched to the geocoded subscriber locations. The systems 20, 22, 24 could also be used in a mode whereby when a subscriber does not respond to communications, the call center 54 is alerted and uses the subscriber's geocoded location to update the call center phone's ALI record to dispatch emergency responders to the geocoded location. This mode could be useful for people engaging in activities such as scuba diving, skiing, hiking, etc. where there is a potential for the subscriber to become injured but unable to dial an emergency services number. In certain modes, a call center technologist could make the attempts to contact the subscriber and automatically log failed communication attempts on server 60 so that an alarm is triggered if a threshold number of failed communication attempts is exceeded.

In the previous examples, systems 20 and 22 used the triggering of an automatic alarm generated by sensor data to alert a technologist who then initiates the querying of a patient (or subscriber) location database 80 with geocoded locations. However, the system could also be used in a mode in which the patient or subscriber simply calls the call center 54 to initiate the process. In one example, if a person is located in a high rise building in a specific internal location, the typical MSAG addresses for the building would not be specific enough to find the person. If the person were to witness a crime or witness/have a medical emergency, he or she could call the call center 54 to initiate the use of his or her geocoded address to update the call center phone's ALI record, thereby ensuring faster responses by first responders.

The systems and methods disclosed herein may also be used internationally and are in no way limited to any one country. Anyone with a structured schedule can benefit from them. The systems and methods may also be particularly beneficial for those traveling abroad who may be unaware of the emergency services number used in the location of travel. Set forth below are a few non-limiting examples of how the systems and methods described herein may be used.

Example 1

A patient with known cardiac disease requires ECG monitoring and stress testing to determine whether he suffers from acute coronary syndrome. Instead of admitting the patient to a hospital for the required monitoring and testing, he is discharged and fitted with a 12 lead continuous monitoring ECG device, such as the COTTER system supplied by Ross Medical Corporation. The ECG device communicates ECG data to the patients' communication device 32, which in turn communicates the data to the emergency services server 60 via computer network 34. The patient's schedule of activities, including scheduled stress tests, echocardiograms, and Doctor's office visits is input into the patient location database 80 in emergency services database 62. The 12 lead ECG monitor detects changes that occur in myocardial infarction and ischemia, localization of infarcts, right ventricular strain patterns commonly seen in pulmonary embolism, voltage changes seen in pericardial effusion, arrhythmia analysis, heart axis shifts seen in myocardial infarction and pulmonary embolism, electrolyte abnormalities such as hyperkalemia, hypokalemia, drug overdoses with substances like dogoxin and tricyclic antidepressants, pericarditis, fascicular blocks, and ventricular hypertrophy. Using the 12 lead system, a base line condition for the patient is determined and is input into an interpretation server associated with server farm 61. When the interpretation server identifies an alarm condition, an alarm server associated with server farm 61 transmits an alarm to technologist terminal 58 in call center 54. The technologist then initiates a query of the patient location database 80 in the emergency services database 62 to obtain a geocoded location for the patient. The ALI database 52 is updated to associate the geocoded location with the ANI for the call center phone 56. The technologist dials 9-1-1 on the call center phone 56, and the call is routed to the PSAP 40 based on the updated ALI record. The PSAP uses PSAP phone 40 to query the ALI database 52 and obtain the geocoded location. In certain variations, more than 12 ECG leads may be used. In addition, instead of a 12 lead ECG device, and implantable cardioverter defibrillator may be used to measure arrhythmia in a 2 lead system.

In certain implementations, such as those using next generation 911 systems, the patient location database 80 or another database that is linked to it may contain additional information that is used to dynamically update the ALI record for the call center phone 56. Such information may include floor plans for the building in which the patient is located, medical information about the patient, and messages regarding the patient's current condition. Thus, when the PSAP 40 receiving the emergency services call queries ALI database 52, PSAP 40 will receive the patient's MSAG location, floor plans for the building at that location, and medical information about the patient. A message describing the current diagnosis, such as "heart attack" may then be displayed to the PSAP operator.

Example 2

A patient with congestive heart failure requires fluid status monitoring to detect fluid accumulations which may lead into the lungs. Once the body fluid volume reaches a certain point, excessive amounts of fluid enter the lungs, reducing gas exchange and increasing breathing difficulty. Over 3 million people in the US have congestive heart failure, and 30%-40% of them are hospitalized for fear of such fluid accumulations. The patient is provided with a blood vessel impedance monitor to determine fluid status, and his schedule is input in a patient location database 80 of the type described previously. The blood vessel impedance monitor transmits impedance data to the patient's communication device 32, which in turn transmits the data to emergency services server 60 via computer network 34. An interpretation server is configured to trigger different levels of response, including early response (pre-symptom), intermediate response, and late response. In the early response mode, the patient may be contacted by medical responders or alerted on his or her communication device 32 to ensure that they are taking their medications and to make any needed medication and diet changes. In the intermediate response mode, emergency responders are dispatched using system 20 or 22 in the manner described previously based on the patient's geocoded location and provide appropriate non-invasive therapies such as lasix, nitroglycerin, oxygen, etc. In the critical mode, the patient may require intubation and assisted ventilation in an emergency room, and possibly further treatment in an intensive care unit with multiple mediations and potentially invasive monitoring (i.e., central venous lines). Other physiological data devices 30 which may be used to monitor congestive heart failure patients include intra-cardiac pressure sensors, plethysmography sensors, ultrasound, weight scales, and intraarterial pressure sensors.

Example 3

A patient with a low oxygen saturation or hypoxia condition, such as chronic obstructive pulmonary disease, restrictive pulmonary disease, asthma, congestive heart failure or any other condition that prevents adequate oxygen saturation is fitted with a pulse oximeter which transmits oxygen saturation data to patient communication device 32, which in turn transmits the data to emergency services server 60 via computer network 34. An interpretation server that is associated with or included in emergency services server 60 is configured to compare the patient's oxygen saturation data to baseline data and to generate an alarm condition based on a specified deviation from the baseline. The patient's schedule is entered into a patient location data base 80 within or associated with the emergency services server 62. During a low oxygen saturation condition, an interpretation server compares the baseline condition to data received from the pulse oximeter and determines that an alarm condition exists. An alarm server transmits an alarm to the technologist terminal 58 at the call center 54. Based on the data, and/or in consultation with the patient and/or a physician, the technologist causes the geocoded location from patient location database 80 to be transmitted to ALI database 52. The technologist dials 9-1-1, and the call is routed (with the ANI) to the PSAP 40 responsible for the geocoded location. The PSAP 40 queries the ALI system 48 for the patient's geocoded location based on the ANI. The technologist informs the answering PSAP 40 that oxygen delivery and medications are required to treat the patient, which are available in the dispatched ambulance. In a variation of this example, personnel with prolonged exposure to carbon monoxide can be provided CO-oximeters to detect carbon monoxide levels in the blood and to provide emergency services when detected levels deviate by a specified amount from a baseline condition.

Example 4

Uncontrolled diabetes has many associated acute and chronic complications. Self-monitoring blood glucose levels can be difficult for many patients which can lead to life threatening complications. Patients with continuously elevated blood glucose levels may develop diabetic ketoacidosis, hyperosmolar hyperglycemic non-ketotic coma, and infections. In this example, a patient is provided with a glucometer that is configured to transmit glucose data to patient communication device 32 which is in turn configured to transmit the data to emergency services server 60 via computer network 34. Certain known glucometers are implantable and/or Bluetooth enabled, such as the Myglucohealth® wireless meter supplied by Entra Health Systems LLC of San Diego, Calif. Baseline glucose data is obtained and saved in a medical record database associated with an interpretation server. The interpretation server receives glucose data from the patient and determines whether it deviates by a specified amount from the baseline data, in which case an alarm is transmitted to technologist terminal 58. The patient's schedule is entered into a patient location database 80. When the interpretation server detects an alarm condition, the technologist terminal 58 receives an alarm. The technologist causes emergency services server 60 to transmit the patient's geocoded location to the ALI server 52. The technologist dials 9-1-1, and the call is routed to the PSAP 40 in the patient's jurisdiction. The PSAP 40 transmits the ANI received with the call to the ALI system 28 and retrieves an ALI record indicating the patient's current location, which is displayed on PSAP terminal 44. Emergency responders are dispatched to the patient's location and provide glucose (in the case of hypoglycemia), and/or other medications indicated for the patient's condition. Certain glucometers also measure hemoglobin levels and can be used for this purpose to detect low hemoglobin (anemia) levels. Low hemoglobin is often the result of bleeding which can go undetected until hemoglobin levels are dangerously low, as in the cases of cirrhosis or peptic ulcer disease. For patients with low hemoglobin levels but who do not have blood glucose regulatory problems, hemoglobin alone can be measured.

Example 5

Electroencephalography (EEG) is gaining in popularity in detecting neurological derangements associated with brain cell ischemia during stroke. Some studies suggest that these derangements precede symptoms. Other studies have correlated specific findings on EEG readings, such as the presence of delta waves, to areas of the brain that are acutely ischemic. Current research is cost prohibitive because it would require long term EEG monitoring in a hospital. In this example, a patient is provided with an EEG device configured to transmit EEG data to patient communication device 32. Baseline data are generated and used to generate alarms transmitted to technologist 58 in the manner described previously. The alarms may be used to develop algorithms for predicting the onset of stroke or transient ischemic attack and to dispatch first responders to the patient when such an event is imminent. In addition, EEG monitoring can be used to track seizure activity and reduce the neurological damage resulting from such seizures by using the geocoding techniques described herein to quickly dispatch first responders to the patient's location.

Example 6

Patients who have undergone aortic aneurism repair using endovascular grafts may need monitoring to ensure that the graphs do not fail. Increased pressure between the walls of the aortic repair may indicate repair and wall breakdown and could lead to aneurysm rupture, which is life threatening. Monitoring and reducing intravascular pressures reduces the chance of endovascular graph failure. Thus, in this example, a patient is provided with an endovascular graph pressure sensor which wirelessly transmits pressure data to the patient communication device 32, which in turn transmits the data to emergency services server 60. The patient's schedule is entered into a patient location database 80, and when the sensor indicates a possible medical emergency event (as determined by an interpretation server), first responders are dispatched to the patient's geocoded location by a call center technologist in the manner described previously.

As indicated in the foregoing examples, a number of different physiological data devices 32 may be used to monitor a number of different types of physiological data. Other conditions that could be monitored include chest pains, shortness of breath, jaw pain, arm pain, leg pain, abdominal pain, diaphoresis, syncope, lightheadedness, swelling, and focal neurological deficits. The following examples describe other scenarios in which systems 20 and 22 and the geocoding techniques described herein may be beneficially used.

Example 7

A number of disaster emergency response subscribers provide schedule information which is input into a subscriber location database similar to the patient location database 80 of FIG. 2. The subscriber location database is part of or associated with emergency services server 62. During a natural disaster, call center 54 obtains information about the nature of the natural disaster and its geographic boundaries. A server associated with server farm 61 is programmed to determine which subscribers lie within the geographic boundaries of the affected area. Subscriber communication devices (such as patient communication devices 32) comprise smart phones with sensors (e.g., video sensors, speaker phone, pressure sensors, depth sensors, movement sensors, heat sensors, electrical sensors) which can detect and confirm that the subscriber is proximate the communication device. The communication devices provide preliminary location information (e.g., a time-stamp of a transmission with GPS coordinates or radiolocation coordinates) to emergency services server 61. Using the preliminary location information, the subscriber location database is queried to obtain a geocoded location (e.g., using the method of FIG. 5) for the first subscriber believed to be proximate his or her communication device. The geocoded location is used to update ALI database 52. The technologist dials 9-1-1, and the call is routed to the PSAP 40 responsible for the geocoded location. The PSAP 40 then uses the ANI for call center phone 56 to query the ALI database 52 and obtain the first subscriber's geocoded location, which is then provided to PSAP terminal 58 by selective routing switch 66. Emergency responders are then dispatched to the subscriber, and the process is repeated for the other subscribers lying within the area affected by the disaster. In one variant, the time of the disaster is used as a time-stamp to query the subscriber location database for a geocoded location instead of using a time-stamp received from a subscriber communication device.

Example 8

A family subscribes to a home security service that uses the system 20 of FIG. 20. The family plans on traveling abroad and provides its travel schedule, which is then entered into a subscriber location database similar to the patient location database 80 of FIG. 2. While abroad, the family stays in a rented residence and uses a burglar alarm which transmits an alarm to a subscriber communication device (similar to patient communication device 32), which in turn transmits the alarm data to emergency services server 61 along with an associated time-stamp. Alternatively, the alarm device may transmit alarm data to network 34 and server 60 without the use of the patient communication device. If a time-stamp cannot be provided, server 60 can use the time of receipt of the alarm data for purposes of querying the subscriber location database. The subscriber location database indicates that the family is in the rented residence. The technologist transmits the geocoded location to ALI database 52 to associate the geocoded location with the call center phone 56. The technologist dials the emergency services number for the jurisdiction in which the family is staying (e.g., 112 if the family is in Spain) and communicates with the local PSAP to obtain assistance for the family. Local law enforcement is then dispatched to the residence.

Example 9

A subscriber is sailing in the ocean, and a storm overtakes his boat. Emergency services server 60 is programmed to receive data concerning natural disasters in the area in which subscriber is sailing and receives an alert that one has occurred. The subscriber provides schedule information such as the course and location of his voyage which is entered in a subscriber location database. A technologist in call center 54 is alerted to the storm and queries the emergency services server 60 for the subscriber's geocoded location based on the time-stamp of the alert. The geocode algorythm would be similar to the one depicted if FIG. 8 where transit path is used to locate the subscriber. If the technologist can reach the subscriber, he contacts the subscriber on the subscriber communication device 32 to confirm the subscriber's location. Otherwise, the technologist causes emergency services server 60 to transmit the geocoded location to the ALI database 52. The ALI database 52 is updated so that the call center phone 56 ANI is associated with the geocoded location. The technologist dials the emergency services number for the geocoded location, and the call is routed to the local PSAP 40. The local PSAP 40 queries the ALI system 48 using the ANI and receives a message identifying the geocoded location on terminal 44. The PSAP dispatches emergency responders to the geocoded location.

Example 10

A subscriber goes scuba diving off the coast of France. Before leaving, he provides his diving schedule which is entered into a subscriber location database within or associated with emergency services database 62. His diving computer is wirelessly connected to computer network 34 and communicates information related to the dive to emergency services server 60. During the dive, the subscriber becomes trapped below the surface. A low oxygen alarm is triggered by the diving computer and is communicated to the emergency services server 60, which in turn communicates the alarm to call center 54. Based on the time of receipt of the alarm, the technologist queries the subscriber location database to obtain the subscriber's geocoded location. The technologist causes emergency services server 60 to transmit the geocoded location (which may be a longitude and latitude in this example) to the ALI database 52. The technologist dials the emergency services number for France, and the call is routed to the PSAP responsible for the geocoded location, which then dispatches emergency responders to rescue the diver.

Example 11

An attorney works in a high rise office building in a large city. The building has an MSAG address in its jurisdiction, but none of its floors or offices have their own distinct MSAG addresses. The attorney provides his schedule information which includes the internal floors and offices at which he can routinely be found, as well as those at which he might be found (e.g., unscheduled locations). The schedule information is entered into a subscriber location database. During a meeting, the attorney's client has a heart attack. The attorney calls the call center 54 with his subscriber communication device 32. The technologist uses the time-stamp of the call to query the subscriber location database. Although he is on the phone, the attorney cannot confirm his internal floor or office in the building. The ALI database 52 is updated so that the call center phone's 56 ANI is associated with the geocoded location, i.e., the building, floor, and office at which the attorney is predicted to be located. The technologist dials 911, and the call is routed to the PSAP 40 in the building's jurisdiction. The PSAP 40 queries the ALI system 48 with the ANI and receives the geocoded location, including the building address, floor, and office. Emergency responders are dispatched to the geocoded location and do not have to guess or use other means to ascertain where the attorney and his client are located.

Example 12

A subscriber goes on a trip to a relative's home and provides her schedule information which is entered into the subscriber location database. She also brings with her a portable carbon monoxide and smoke detector which is configured to wirelessly communicate with computer network 34, either directly or via subscriber communication device 32. A fire breaks out in the middle of the night, and the subscriber's detector generates an alarm which is transmitted to emergency services server 60. A call center technologist receives the alarm and initiates a query of the subscriber location database to obtain the subscriber's current geocoded location. The technologist attempts to but cannot reach the subscriber on her communication device 32. The technologist transmits the geocoded location to the selective routing switch 66 in the manner described previously and calls 9-1-1. The 9-1-1 call is routed to the PSAP responsible for the geocoded location, and emergency responders are dispatched to the relative's home.

The foregoing examples are meant to be illustrative only. The systems and methods described herein can be used in a variety of other applications, including those in which subscribers or patients are traveling or mobile and have a defined schedule that can be used to geocode their locations.

What is claimed is:

1. A system for a medical services provider having a phone to provide emergency services to a person with whom the medical services provider is communicating regarding a medical condition, wherein the person is located in a first geographic zone serviced by a first emergency services dispatcher, and the phone is located outside the first geographic zone, the system comprising:
    an emergency services server programmed to update location field data in an automatic location identification database record for the phone with location data describing the person's location;
    a selective routing database, wherein when the location field data in the automatic location identification database record for the phone is updated to the location data describing the person's location, the selective routing database is updated such that when a call is placed by entering an emergency services number into the phone while the phone is located outside the first geographic zone, and while at the same time the person is located in the first geographic zone, the call is routed to the first emergency services dispatcher.

2. The system of claim 1, wherein the emergency services number corresponds to at least one of a jurisdiction in which the phone is located and a nature of requested services.

3. The system of claim 2, wherein the emergency services number corresponds to both the jurisdiction in which the phone is located and a nature of requested services.

4. The system of claim 1, where the phone is a VoIP phone.

5. The system of claim 1, wherein the phone is connected to a branch exchange, the branch exchange is connected to a plurality of emergency services dispatchers, and wherein when the location field data in the automatic location identification record for the phone is updated, the call is routed to a public safety answering point, and the public safety answering point is the first emergency services dispatcher.

6. The system of claim 1, wherein the emergency services server is programmed to determine the location data describing the person's location by comparing a time-stamp defining a time at which it is desired to locate the person to a plurality of database time entries corresponding to the person and determining whether any of the plurality of database time entries corresponding to the person are within a pre-selected time increment from the time-stamp.

7. The system of claim 6, further comprising a location database, wherein the location database comprises database identity information for a plurality of people and one or more database locations for each person from among the plurality of people.

8. The system of claim 1, wherein the selective routing database comprises a correlation of at least one of an automatic number information (ANI) value and a pseudo-automatic number information (p-ANI) value for the phone to a corresponding database public safety answering point from among a plurality of public safety answering points, and when the location field data in the automatic location identification database record for the phone is updated to the location data describing the person's location, the correlation is updated so that the database public safety answering point is the first emergency services dispatcher.

9. The system of claim 1, wherein the emergency services server is programmed to determine the location data describing the person's location based on a time-stamp, wherein the time-stamp is data indicative of a date, day of the week, and/or time of day for which a person's location is sought.

10. The system of claim 1, wherein the phone and the person are located at different addresses.

11. A method for a medical services provider having a phone to provide emergency services to a person with whom the medical services provider is communicating regarding a medical condition, wherein the person is located in a first geographic zone serviced by a first emergency services dispatcher, and the phone is located outside the first geographic zone, the method comprising:
updating location field data in an automatic location database record for the phone with location data describing the person's location;
updating a selective routing database such that when a call is placed by entering an emergency services number into the phone while the phone is located outside the first geographic zone, and while at the same time the person is located in the first geographic zone, the call is routed to the first emergency services dispatcher.

12. The method of claim 11, wherein the emergency services number corresponds to at least one of a jurisdiction in which the phone is located and a nature of requested services.

13. The method of claim 11, wherein the emergency services number corresponds to both the jurisdiction in which the phone is located and a nature of requested services.

14. The method of claim 11, wherein the phone is a VoIP phone.

15. The method of claim 11, wherein the phone is connected to a branch exchange, and the branch exchange is connected to a plurality of emergency services dispatchers via a selective routing switch, and when the selective routing database is updated, the call is routed by the selective routing switch to the first emergency services dispatcher.

16. A method for medical services personnel having a phone to provide improved emergency services to a patient, the method comprising:
receiving medical physiologic data from the patient indicating the occurrence of a medical event, wherein the patient is located in a first geographic zone serviced by a first emergency services dispatcher;
determining data describing the patient's location, wherein the data describing the patient's location comprises an address at which the patient is located; and
updating location field data in an automatic location identification database record for the phone with the determined data describing the patient's location, wherein the phone is located outside the first geographic zone, wherein when a call is placed by
entering a predetermined emergency services number into the phone, the call is routed to the first emergency services dispatcher.

17. The method of claim 16, wherein the emergency services dispatcher is a public safety answering point.

18. The method of claim 16, wherein the emergency services number corresponds to at least one of a jurisdiction in which the phone is located and a nature of requested services.

19. The method of claim 16, wherein the emergency services number corresponds to both the jurisdiction in which the phone is located and a nature of requested services.

20. The method of claim 16, wherein the phone is a VoIP phone.

21. The method of claim 16, wherein the phone is connected to a branch exchange, the branch exchange is connected to a plurality of emergency services dispatchers via a selective routing switch.

22. A system for a medical services provider having a phone to provide emergency services to a patient with whom the medical services provider is communicating regarding a medical condition, wherein the patient is located in a first geographic zone serviced by a first emergency services dispatcher, and the phone is outside the first geographic zone, the system comprising:
a patient location database comprising a plurality of database time entries and a plurality of database patient locations, wherein each of the database time entries corresponds to a patient, and each database patient location comprises location data describing a location for the patient which corresponds to a database patient time entry;
an emergency services server programmed to identify the occurrence of a medical event based on received medical physiologic data from the patient and reference medical physiologic data and further programmed to determine location data describing a location for the patient in the first geographic zone from a time-stamp and to update location field data in an automatic location identification database record for the phone with the determined location data describing a location for the patient in the first geographic zone, wherein when a designated emergency services number is entered into the phone, a call is placed to the first emergency services dispatcher.

23. The system of claim 22, wherein the designated emergency services number corresponds to at least one of a jurisdiction in which the phone is located and a nature of requested emergency services.

24. The system of claim 23, wherein the designated emergency services number corresponds to both of the jurisdiction in which the phone is located and the nature of the requested emergency services.

25. The system of claim 22, wherein the phone is connected to a branch exchange, the branch exchange is connected to a plurality of emergency services dispatchers via a selective routing switch.

* * * * *